United States Patent
Meade et al.

(10) Patent No.: US 9,962,156 B2
(45) Date of Patent: May 8, 2018

(54) SUTURING NEEDLE

(71) Applicant: ENDOEVOLUTION, LLC, Raynham, MA (US)

(72) Inventors: John C. Meade, Mendon, MA (US); Douglas M. MacArthur, Acton, MA (US); Stephen M. Blinn, Amherst, NH (US); Christopher Sauliner, Brunswick, ME (US); Brian R. Edwards, Raymond, ME (US); Gerald I. Brecher, North Andover, MA (US)

(73) Assignee: EndoEvolution, LLC, Raynham, MA (US)

( * ) Notice: Subject to any disclaimer, the term of this patent is extended or adjusted under 35 U.S.C. 154(b) by 0 days. days.

(21) Appl. No.: 15/256,079

(22) Filed: Sep. 2, 2016

(65) Prior Publication Data

US 2017/0049442 A1 Feb. 23, 2017

Related U.S. Application Data

(63) Continuation of application No. 13/900,991, filed on May 23, 2013, now abandoned, which is a (Continued)

(51) Int. Cl.
*A61B 17/04* (2006.01)
*A61B 17/06* (2006.01)
(Continued)

(52) U.S. Cl.
CPC ...... *A61B 17/0491* (2013.01); *A61B 17/0482* (2013.01); *A61B 17/062* (2013.01);
(Continued)

(58) Field of Classification Search
CPC ............ A61B 17/0482; A61B 17/0491; A61B 17/06114; A61B 17/062; A61B 17/04;
(Continued)

(56) References Cited

U.S. PATENT DOCUMENTS

| 1,327,577 A | 1/1920 | Turner |
| 1,822,330 A | 9/1931 | Ainslie |

(Continued)

FOREIGN PATENT DOCUMENTS

| CN | 2169381 | 6/1994 |
| CN | 201082170 | 7/2008 |

(Continued)

OTHER PUBLICATIONS

Decision of Refusal issued in JP Application No. 2015-112857, dated Dec. 8, 2016, 3 pages.
(Continued)

*Primary Examiner* — Dianne Dornbusch
(74) *Attorney, Agent, or Firm* — Crawford Maunu PLLC

(57) ABSTRACT

A tissue closure device includes a pusher assembly having a drive arm extending from a drive shaft and a drive mechanism at a distal end of the drive arm, wherein the drive mechanism is capable of releasably engaging and rotating a suturing needle having a pointed end and a blunt end about a rotational axis and a cartridge having a protective housing and the suturing needle, the cartridge extending from a distal end of a cartridge holder assembly and releasably attached to the cartridge holder assembly. A pointed end of the suturing needle may be positioned within the protective housing before and after a complete rotation of the suturing needle about the rotational axis. A removable electronic module may be provided controlled by an actuator that mechanically engages the drive shaft to rotate the drive shaft and the drive mechanism, thereby rotating the suturing needle about the rotational axis.

11 Claims, 38 Drawing Sheets

Related U.S. Application Data continuation of application No. 12/218,633, filed on Jul. 17, 2008, now Pat. No. 8,469,973, which is a continuation of application No. PCT/US2007/002204, filed on Jan. 29, 2007.

(60) Provisional application No. 60/763,038, filed on Jan. 27, 2006.

(51) Int. Cl.
*A61B 17/062* (2006.01)
*A61B 17/00* (2006.01)
*A61B 34/00* (2016.01)
*A61B 90/00* (2016.01)

(52) U.S. Cl.
CPC ........ *A61B 17/06114* (2013.01); *A61B 34/70* (2016.02); *A61B 2017/00398* (2013.01); *A61B 2017/00734* (2013.01); *A61B 2017/06028* (2013.01); *A61B 2017/06052* (2013.01); *A61B 2090/0813* (2016.02)

(58) Field of Classification Search
CPC .............. A61B 17/0469; A61B 17/047; A61B 17/0483; A61B 2017/06052; A61B 2017/00398; A61B 2017/00734; A61B 2017/06028

See application file for complete search history.

(56) References Cited

U.S. PATENT DOCUMENTS

| | | | |
|---|---|---|---|
| 2,327,353 | A | 8/1943 | Karle |
| 2,601,564 | A | 6/1952 | Smith |
| 3,197,997 | A | 8/1965 | Kurtz |
| 3,311,110 | A | 3/1967 | Sol et al. |
| 3,344,790 | A | 10/1967 | Dorner |
| 3,762,418 | A | 10/1973 | Wasson |
| 3,834,599 | A | 9/1974 | Herr |
| 3,835,912 | A | 9/1974 | Kristensen et al. |
| 3,910,282 | A | 10/1975 | Messer et al. |
| 3,951,261 | A | 4/1976 | Mandel et al. |
| 3,972,418 | A | 8/1976 | Schuler et al. |
| 4,027,608 | A | 6/1977 | Arbuckle |
| 4,235,177 | A | 11/1980 | Arbuckle |
| 4,331,277 | A | 5/1982 | Green |
| 4,437,465 | A | 3/1984 | Nomoto et al. |
| 4,509,945 | A | 4/1985 | Kramann et al. |
| 4,527,564 | A | 7/1985 | Eguchi et al. |
| 4,557,265 | A | 12/1985 | Andersson |
| 4,621,640 | A | 11/1986 | Mulhollan et al. |
| 4,759,348 | A | 7/1988 | Cawood |
| 4,841,888 | A | 6/1989 | Mills et al. |
| 4,899,746 | A | 2/1990 | Brunk |
| 4,957,502 | A | 9/1990 | Takase |
| 5,080,663 | A | 1/1992 | Mills et al. |
| 5,089,012 | A | 2/1992 | Prou |
| 5,201,760 | A | 4/1993 | West |
| 5,210,376 | A | 5/1993 | Caviar |
| 5,269,806 | A | 12/1993 | Sardelis et al. |
| 5,305,281 | A | 4/1994 | Lubeck |
| 5,306,281 | A | 4/1994 | Beurrier |
| 5,308,353 | A | 5/1994 | Beurrier |
| 5,318,578 | A | 6/1994 | Hasson |
| 5,344,061 | A | 9/1994 | Crainich |
| 5,358,498 | A | 10/1994 | Shave |
| 5,364,408 | A | 11/1994 | Gordon |
| 5,373,101 | A | 12/1994 | Barabolak |
| 5,376,101 | A | 12/1994 | Green et al. |
| 5,387,221 | A | 2/1995 | Bisgaard |
| 5,437,681 | A | 8/1995 | Meade et al. |
| 5,462,558 | A | 10/1995 | Kolesa et al. |
| 5,472,081 | A | 12/1995 | Kilgrow et al. |
| 5,474,568 | A | 12/1995 | Scott |
| 5,478,344 | A | 12/1995 | Stone et al. |
| 5,478,345 | A | 12/1995 | Stone et al. |
| 5,480,409 | A | 1/1996 | Riza |
| 5,503,266 | A | 4/1996 | Kalbfeld et al. |
| 5,514,159 | A | 5/1996 | Matula et al. |
| 5,540,705 | A | 7/1996 | Meade et al. |
| 5,571,119 | A | 11/1996 | Atala |
| 5,575,800 | A | 11/1996 | Gordon |
| 5,578,044 | A | 11/1996 | Gordon et al. |
| 5,643,295 | A | 7/1997 | Yoon |
| 5,645,552 | A | 7/1997 | Sherts |
| 5,665,096 | A | 9/1997 | Yoon |
| 5,665,109 | A | 9/1997 | Yoon |
| 5,669,490 | A | 9/1997 | Colligan et al. |
| 5,675,961 | A | 10/1997 | Cerwin et al. |
| 5,709,693 | A | 1/1998 | Taylor |
| 5,713,910 | A | 2/1998 | Gordon et al. |
| 5,715,942 | A | 2/1998 | Li et al. |
| 5,716,369 | A | 2/1998 | Riza |
| 5,741,277 | A | 4/1998 | Gordon et al. |
| 5,755,729 | A | 5/1998 | de la Torre et al. |
| 5,759,188 | A | 6/1998 | Yoon |
| 5,766,186 | A | 6/1998 | Faraz et al. |
| 5,814,069 | A | 9/1998 | Schulze et al. |
| 5,814,071 | A | 9/1998 | McDevitt et al. |
| 5,833,695 | A | 11/1998 | Yoon |
| 5,860,992 | A | 1/1999 | Daniel et al. |
| 5,891,160 | A | 4/1999 | Williamson, IV et al. |
| 5,906,273 | A | 5/1999 | Pohle et al. |
| 5,908,426 | A | 6/1999 | Pierce |
| 5,908,428 | A | 6/1999 | Scirica et al. |
| 5,911,727 | A | 6/1999 | Taylor |
| 5,954,733 | A | 9/1999 | Yoon |
| 5,968,077 | A | 10/1999 | Wojciechowicz et al. |
| 5,993,466 | A | 11/1999 | Yoon |
| 6,016,905 | A | 1/2000 | Gemma et al. |
| 6,036,694 | A | 3/2000 | Goble et al. |
| 6,048,351 | A | 4/2000 | Gordon et al. |
| 6,053,908 | A | 4/2000 | Crainich et al. |
| 6,056,771 | A | 5/2000 | Proto |
| 6,071,289 | A | 6/2000 | Stefanchik et al. |
| 6,096,051 | A | 8/2000 | Kortenbach et al. |
| 6,126,666 | A | 10/2000 | Trapp et al. |
| 6,135,385 | A | 10/2000 | Martinez de Lahidalga |
| 6,136,010 | A | 10/2000 | Modesitt et al. |
| 6,159,224 | A | 12/2000 | Yoon |
| 6,261,307 | B1 | 7/2001 | Yoon et al. |
| 6,270,508 | B1 | 8/2001 | Klieman et al. |
| 6,322,581 | B1 | 11/2001 | Fukuda et al. |
| 6,332,888 | B1 | 12/2001 | Levy et al. |
| 6,346,111 | B1 | 2/2002 | Gordon et al. |
| 6,443,962 | B1 | 9/2002 | Gaber |
| 6,454,777 | B1 | 9/2002 | Green |
| 6,454,778 | B2 | 9/2002 | Kortenbach |
| 6,494,888 | B1 | 12/2002 | Laufer et al. |
| 6,506,196 | B1 | 1/2003 | Laufer |
| 6,558,400 | B2 | 5/2003 | Deem et al. |
| 6,656,194 | B1 | 12/2003 | Gannoe et al. |
| 6,663,639 | B1 | 12/2003 | Laufer et al. |
| 6,719,763 | B2 | 4/2004 | Chung et al. |
| 6,719,764 | B1 | 4/2004 | Gellman et al. |
| 6,746,460 | B2 | 6/2004 | Gannoe et al. |
| 6,755,843 | B2 | 6/2004 | Chung et al. |
| 6,835,200 | B2 | 12/2004 | Laufer et al. |
| 6,877,352 | B1 | 4/2005 | Schlereth |
| 6,908,427 | B2 | 6/2005 | Fleener et al. |
| 6,923,819 | B2 | 8/2005 | Meade et al. |
| 6,955,643 | B2 | 10/2005 | Gellman et al. |
| 7,004,951 | B2 | 2/2006 | Gibbens, III |
| 7,033,370 | B2 | 4/2006 | Gordon et al. |
| 7,041,111 | B2 | 5/2006 | Chu |
| 7,144,401 | B2 | 12/2006 | Yamamoto et al. |
| 7,166,116 | B2 | 1/2007 | Lizardi et al. |
| 7,338,504 | B2 | 3/2008 | Gibbens et al. |
| 7,615,060 | B2 | 11/2009 | Stokes et al. |
| 7,628,796 | B2 | 12/2009 | Shelton, IV et al. |
| 7,637,909 | B2 | 12/2009 | Lechot et al. |
| 7,766,925 | B2 | 8/2010 | Stokes et al. |
| 7,828,812 | B2 | 11/2010 | Stokes et al. |

(56) References Cited

U.S. PATENT DOCUMENTS

| | | |
|---|---|---|
| 7,833,236 B2 | 11/2010 | Stokes et al. |
| 7,846,169 B2 | 12/2010 | Shelton, IV et al. |
| 7,862,572 B2 | 1/2011 | Meade et al. |
| 7,887,554 B2 | 2/2011 | Stokes et al. |
| 7,976,533 B2 | 7/2011 | Larsson |
| 7,976,555 B2 | 7/2011 | Meade et al. |
| 7,993,354 B1 | 8/2011 | Brecher et al. |
| 8,066,737 B2 | 11/2011 | Meade et al. |
| 8,123,764 B2 | 2/2012 | Meade et al. |
| 8,469,973 B2 | 6/2013 | Meade et al. |
| 8,500,756 B2 | 8/2013 | Papa et al. |
| 8,623,048 B2 | 1/2014 | Brecher et al. |
| 8,641,728 B2 | 2/2014 | Stokes et al. |
| 8,702,732 B2 | 4/2014 | Woodard, Jr. et al. |
| 8,906,043 B2 | 12/2014 | Woodard, Jr. et al. |
| 9,125,645 B1 | 9/2015 | Martin et al. |
| 9,173,655 B2 | 11/2015 | Martin |
| 9,220,496 B2 | 12/2015 | Martin et al. |
| 9,357,998 B2 | 6/2016 | Martin et al. |
| 9,370,354 B1 | 6/2016 | Martin et al. |
| 9,375,212 B2 | 6/2016 | Martin et al. |
| 9,398,905 B2 | 7/2016 | Martin |
| 9,427,226 B2 | 8/2016 | Martin et al. |
| 9,427,227 B2 | 8/2016 | Martin et al. |
| 9,445,807 B2 | 9/2016 | Brecher et al. |
| 9,451,948 B2 | 9/2016 | Meade et al. |
| 9,474,522 B2 | 10/2016 | Deck et al. |
| 9,474,523 B2 | 10/2016 | Meade et al. |
| 9,486,209 B2 | 11/2016 | Martin et al. |
| 9,498,207 B2 | 11/2016 | Martin et al. |
| 9,526,495 B2 | 12/2016 | Martin et al. |
| 2002/0107530 A1 | 8/2002 | Sauer et al. |
| 2002/0116011 A1 | 8/2002 | Chee Chung et al. |
| 2002/0173800 A1 | 11/2002 | Dreyfuss et al. |
| 2002/0193809 A1 | 12/2002 | Meade et al. |
| 2002/0198542 A1 | 12/2002 | Yamamoto et al. |
| 2003/0083674 A1 | 5/2003 | Gibbens |
| 2003/0105475 A1 | 6/2003 | Sancoff et al. |
| 2003/0171760 A1 | 9/2003 | Gambale |
| 2003/0181924 A1 | 9/2003 | Yamamoto et al. |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0034372 A1 | 2/2004 | Chu |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0181243 A1 | 9/2004 | Chu et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens et al. |
| 2005/0035007 A1 | 2/2005 | Kennedy et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |
| 2005/0262984 A1 | 12/2005 | Hetcher et al. |
| 2006/0069396 A1 | 3/2006 | Meade et al. |
| 2006/0111732 A1 | 5/2006 | Gibbens et al. |
| 2006/0224184 A1 | 10/2006 | Stefanchik et al. |
| 2006/0282089 A1 | 12/2006 | Stokes et al. |
| 2006/0282090 A1 | 12/2006 | Stokes et al. |
| 2006/0282091 A1 | 12/2006 | Shelton et al. |
| 2006/0282092 A1 | 12/2006 | Stokes et al. |
| 2006/0282093 A1 | 12/2006 | Shelton et al. |
| 2006/0282094 A1 | 12/2006 | Stokes et al. |
| 2006/0282095 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1 | 12/2006 | Shelton et al. |
| 2006/0282099 A1 | 12/2006 | Stokes et al. |
| 2007/0135838 A1 | 6/2007 | Meyer |
| 2008/0132919 A1 | 6/2008 | Chui et al. |
| 2008/0140091 A1 | 6/2008 | DeDeyne et al. |
| 2009/0024145 A1 | 1/2009 | Meade et al. |
| 2010/0036415 A1 | 2/2010 | Cabezas |
| 2010/0049219 A1 | 2/2010 | Cronin et al. |
| 2010/0130990 A1 | 5/2010 | Saliman |
| 2010/0152751 A1 | 6/2010 | Meade et al. |
| 2014/0171977 A1 | 6/2014 | Martin et al. |
| 2014/0171979 A1 | 6/2014 | Martin et al. |
| 2014/0172015 A1 | 6/2014 | Martin et al. |
| 2015/0133967 A1 | 5/2015 | Martin |
| 2015/0351745 A1 | 12/2015 | Mumaw et al. |
| 2015/0351746 A1 | 12/2015 | Martin et al. |
| 2015/0351749 A1 | 12/2015 | Martin et al. |
| 2015/0351756 A1 | 12/2015 | Martin et al. |
| 2016/0317148 A1 | 11/2016 | Martinez |
| 2016/0331374 A1 | 11/2016 | Martin et al. |
| 2016/0345958 A1 | 12/2016 | Martin et al. |
| 2016/0346827 A1 | 12/2016 | Martin et al. |
| 2016/0361055 A1 | 12/2016 | Martin et al. |
| 2016/0367238 A1 | 12/2016 | Deck et al. |
| 2016/0367239 A1 | 12/2016 | Mumaw et al. |
| 2016/0367240 A1 | 12/2016 | Shelton, IV et al. |
| 2016/0367243 A1 | 12/2016 | Martin et al. |

FOREIGN PATENT DOCUMENTS

| | | |
|---|---|---|
| DE | 4310315 | 10/1993 |
| EP | 0648474 | 4/1995 |
| EP | 2103262 | 9/2009 |
| EP | 2292157 | 3/2011 |
| EP | 2308391 | 4/2011 |
| EP | 2370002 | 10/2011 |
| EP | 1791476 | 12/2015 |
| FR | 2540377 | 8/1984 |
| GB | 18602 | 9/1908 |
| JP | 556270 | 1/1980 |
| JP | 55151956 | 11/1980 |
| JP | 07178100 | 7/1995 |
| JP | 07328021 | 12/1995 |
| JP | H11276492 | 10/1999 |
| JP | 2000139931 | 5/2000 |
| JP | 2005080761 | 3/2005 |
| JP | 2005253987 | 9/2005 |
| WO | WO9729694 | 8/1997 |
| WO | WO9912482 | 3/1999 |
| WO | WO9940850 | 8/1999 |
| WO | WO9947050 | 9/1999 |
| WO | WO0112084 | 2/2001 |
| WO | 2002102226 | 12/2002 |
| WO | WO02102226 | 12/2002 |
| WO | WO03028541 | 10/2003 |
| WO | WO2004012606 | 2/2004 |
| WO | WO2004021894 | 3/2004 |
| WO | WO2004028402 | 4/2004 |
| WO | WO2004086986 | 10/2004 |
| WO | WO2006034209 | 3/2006 |
| WO | WO2007089603 | 8/2007 |
| WO | WO2008147555 | 12/2008 |
| WO | WO2010062380 | 6/2010 |

OTHER PUBLICATIONS

Non-Final Office Action in U.S. Appl. No. 15/260,094, dated Jan. 17, 2017, 14 pages.

Preliminary Amendment filed in U.S. Appl. No. 15/260,094, dated Nov. 18, 2016, 7 pages.

International Preliminary Report on Patentability dated Jan. 13, 2008 and Written Opinion dated Jun. 13, 2008 for PCT/US05/33507.

International Preliminary Report on Patentability dated Jan. 27, 2006 and Written Opinion dated Nov. 1, 2007 for PCT/US07/02204.

International Search Report and Written Opinion dated Mar. 3, 2003 for PCT/US02/12560.

(56) References Cited

OTHER PUBLICATIONS

International Preliminary Examination Report dated Mar. 12, 2004 for PCT/US02/12560.
International Search Report and Written Opinion dated Jul. 5, 2010 for PCT/US09/06212.
Supplemental European Search Report dated Mar. 15, 2007 for EP140654.5.
European Search Report dated Feb. 8, 2011 for EP10009831.8.
European Search Report dated Feb. 9, 2011 for EP10009832.6.
Office Action dated Jul. 1, 2014 from Corresponding Japanese Application No. 2013-138559.
European Search Report dated Jun. 5, 2015 from corresponding European Application No. 12822057.1.
European Search Report dated Aug. 14, 2015 from corresponding European Application No. 11830008.
International Search Report issued in related PCT application No. PCT/US07/002204 dated Nov. 1, 2007.
Written Opinion issued in related PCT application No. PCT/US07/002204 dated Nov. 1, 2007.
Search Report dated May 20, 2010 from SG Application No. 200805426-4.
Extended Search Report dated Feb. 17, 2011 from corresponding European Application No. 05797831.4.
Extended Search Report dated Feb. 21, 2011 from corresponding European Application No. 10009831.8.
Extended Search Report dated Feb. 21, 2011 from corresponding European Application No. 10009832.6.
European Search Report dated Mar. 11, 2011 from corresponding European Application No. 07762862.6.
Japanese Office Action dated Oct. 18, 2011 from Corresponding Japanese Application No. 2008-552444.
International Preliminary Report on Patentability dated Feb. 11, 2014 from Corresponding PCT Application Number PCT/US12/049979.
International Search Report and Written Opinion of the International Searching Authority (ISA) dated Apr. 24, 2012 relating to PCT/US11/054334.
Examination Report issued by Hungarian IP Office on behalf of Singapore IP Office issued Feb. 8, 2012 in connection with Singapore Application No. 200907505-2.
Supplementary European Search Report dated Mar. 23, 2007 in connection with EP Application No. 02725747.6.
Supplementary European Search Report dated Oct. 6, 2009 in connection with EP Application No. 02725747.6.
Office Action with English translation in connection with Japanese Patent Application No. JP2007-532595 issued Jan. 4, 2011.
Extended Search Report in connection with EP05797831.4 issued Feb. 25, 2011.
Written Opinion issued Jan. 11, 2011 in connection with Singapore Patent Application No. 200907505-2.
International Search Report and Written Opinion dated Jan. 5, 2009 in connection with PCT/US08/006674.
International Preliminary Report on Patentability dated Nov. 24, 2009 in connection with PCT/US08/006674.
International Search Report issued in related PCT application No. PCT/US09/006212 dated Jul. 5, 2010.
International Search Report issued in related PCT application No. PCT/US05/33507 dated Jun. 13, 2008.
Extended Search Report dated Nov. 29, 2012 from corresponding European Application No. 09829467.1.
Japanese Office Action dated Oct. 18, 2017, from Japanese patent application No. 2016-187970.
Japanese Office Action dated Oct. 18, 2017, from Japanese patent application No. 2016-187970 (English).
U.S. Appl. No. 08/180,662; U.S. Pat. No. 5,437,681, filed Jan. 13, 1994.
U.S. Appl. No. 08/445,359; U.S. Pat. No. 5,540,705, filed May 19, 1995.
U.S. Appl. No. 10/127,254; U.S. Pat. No. 6,923,819, filed Apr. 22, 2002.
U.S. Appl. No. 11/121,810 (abandoned), filed May 4, 2005.
U.S. Appl. No. 11/387,127; U.S. Pat. No. 8,066,737, filed Mar. 22, 2006.
U.S. Appl. No. 13/197,698; U.S. Pat. No. 8,623,048, filed Aug. 3, 2011.
U.S. Appl. No. 13/197,870; U.S. Pat. No. 9,445,807, filed Aug. 4, 2011.
U.S. Appl. No. 15/260,094; U.S. Pat. No. 9,649,107, filed Sep. 8, 2016.
U.S. Appl. No. 15/377,373 (abandoned), filed Dec. 13, 2016.
U.S. Appl. No. 15/377,425 (abandoned), filed Dec. 13, 2016.
U.S. Appl. No. 15/404,394 (abandoned), filed Jan. 12, 2017.
U.S. Appl. No. 15/404,405; U.S. Pat. No. 9,693,770, filed Jan. 12, 2017.
U.S. Appl. No. 15/476,531; U.S. Pat. No. 9,743,923, filed Mar. 31, 2017.
U.S. Appl. No. 15/476,958; U.S. Pat. No. 9,743,925, filed Mar. 31, 2017.
U.S. Appl. No. 15/476,968; U.S. Pat. No. 9,717,495, filed Mar. 31, 2017.
U.S. Appl. No. 15/490,539; U.S. Pat. No. 9,717,493, filed Apr. 18, 2017.
U.S. Appl. No. 15/490,611; U.S. Pat. No. 9,730,688, filed Apr. 18, 2017.
U.S. Appl. No. 15/490,619; U.S. Pat. No. 9,737,296, filed Apr. 18 2017.
U.S. Appl. No. 15/638,412 (pending), filed Jun. 30, 2017.
U.S. Appl. No. 15/640,436 (pending), filed Jun. 30, 2017.
U.S. Appl. No. 15/640,442 (pending), filed Jun. 30, 2017.
U.S. Appl. No. 15/667,459 (pending), filed Aug. 2, 2017.
U.S. Appl. No. 11/231,135; U.S. Pat. No. 7,862,572, filed Sep. 20, 2005.
U.S. Appl. No. 11/982,174 (abandoned), filed Nov. 1, 2007.
U.S. Appl. No. 12/592,174; U.S. Pat. No. 8,123,764, filed Nov. 20, 2009.
U.S. Appl. No. 13/361,444; U.S. Pat. No. 8,821,519, filed Jan. 30, 2012.
U.S. Appl. No. 14/472,254; U.S. Pat. No. 9,451,948, filed Aug. 28, 2014.
U.S. Appl. No. 14/796,642; U.S. Pat. No. 9,474,523, filed Jul. 10, 2015.
U.S. Appl. No. 15/265,650; U.S. Pat. No. 9,597,071, filed Sep. 14, 2016.
U.S. Appl. No. 15/357,375; U.S. Pat. No. 9,700,301, filed Nov. 21, 2016.
U.S. Appl. No. 15/357,533; U.S. Pat. No. 9,700,302, filed Nov. 21, 2016.
U.S. Appl. No. 15/358,210; U.S. Pat. No. 9,642,613, filed Nov. 22, 2016.
U.S. Appl. No. 15/377,502; U.S. Pat. No. 9,642,614, filed Dec. 13, 2016.
U.S. Appl. No. 15/480,561 (pending), filed Apr. 6, 2017.
U.S. Appl. No. 15/480,915 (pending), filed Apr. 6, 2017.
U.S. Appl. No. 15/480,933 (pending), filed Apr. 6, 2017.
U.S. Appl. No. 15/480,945 (pending), filed Apr. 6, 2017.
U.S. Appl. No. 15/640,452 (pending), filed Jun. 30, 2017.
U.S. Appl. No. 15/661,924 (pending), filed Jul. 27, 2017.
U.S. Appl. No. 15/671,450 (pending), filed Aug. 8, 2017.
U.S. Appl. No. 12/218,633; U.S. Pat. No. 8,469,973, filed Jul. 17, 2008.
U.S. Appl. No. 13/900,991 (abandoned), May 23, 2013.
U.S. Appl. No. 15/256,079 (pending), filed Sep. 2, 2016.
U.S. Appl. No. 15/656,655 (pending), filed Jul. 21, 2016.
U.S. Appl. No. 12/175,442; U.S. Pat. No. 7,976,555, filed Jul. 17, 2008.
U.S. Appl. No. 12/909,606; U.S. Pat. No. 7,993,354, filed Oct. 21, 2010.
U.S. Appl. No. 13/204,820 (pending), filed Aug. 8, 2011.
U.S. Appl. No. 13/205,056 (abandoned), filed Aug. 8, 2011.
U.S. Appl. No. 15/377,562 (pending), filed Dec. 13, 2016.
U.S. Appl. No. 15/610,277 (pending), filed May 31, 2017.
Related Application Data for above-referenced U.S. Appl. No. 15/256,079.

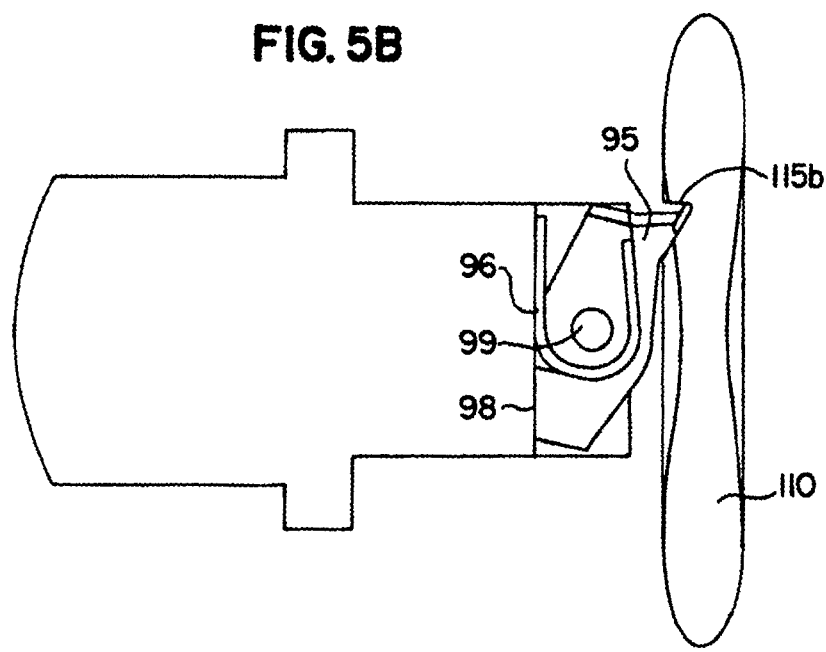
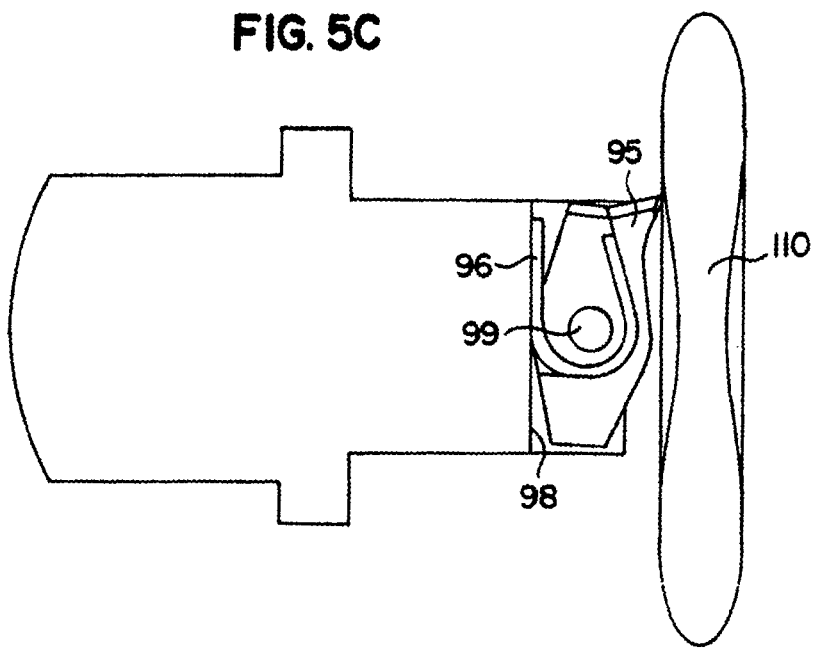

FIG. 22
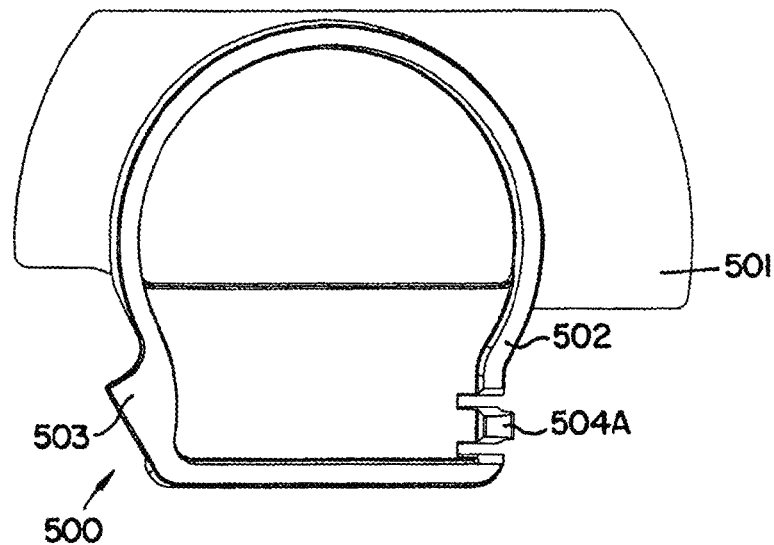
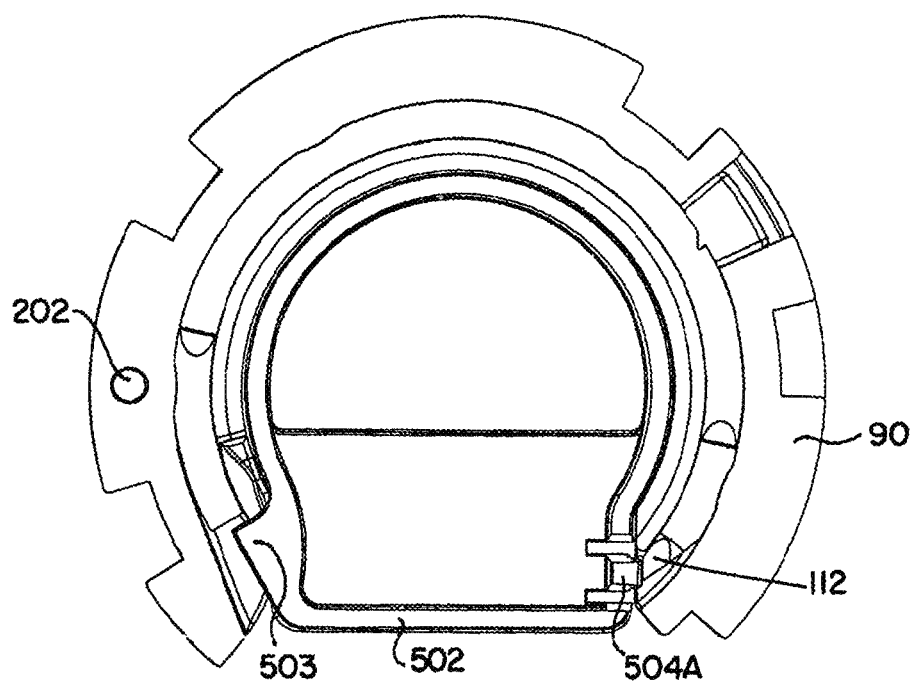
FIG. 23

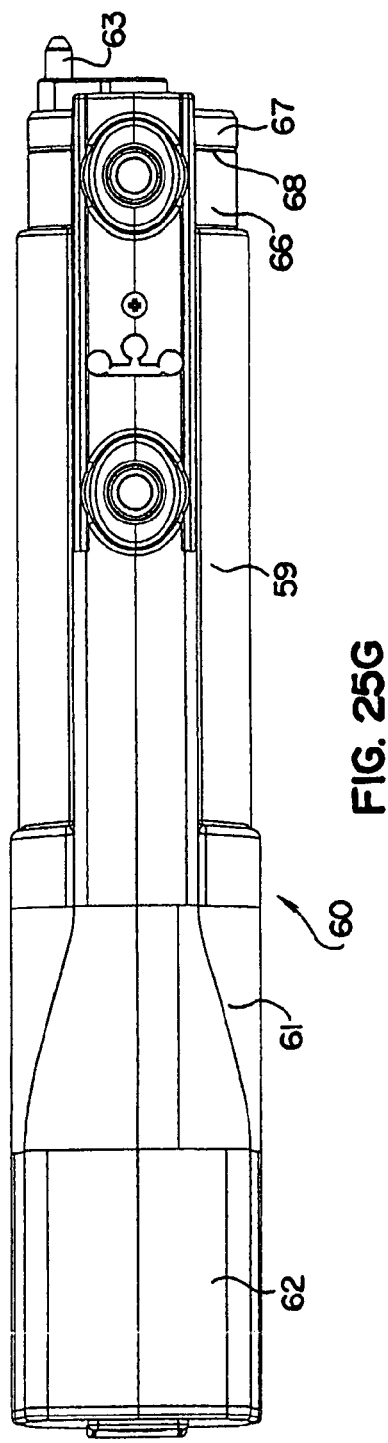
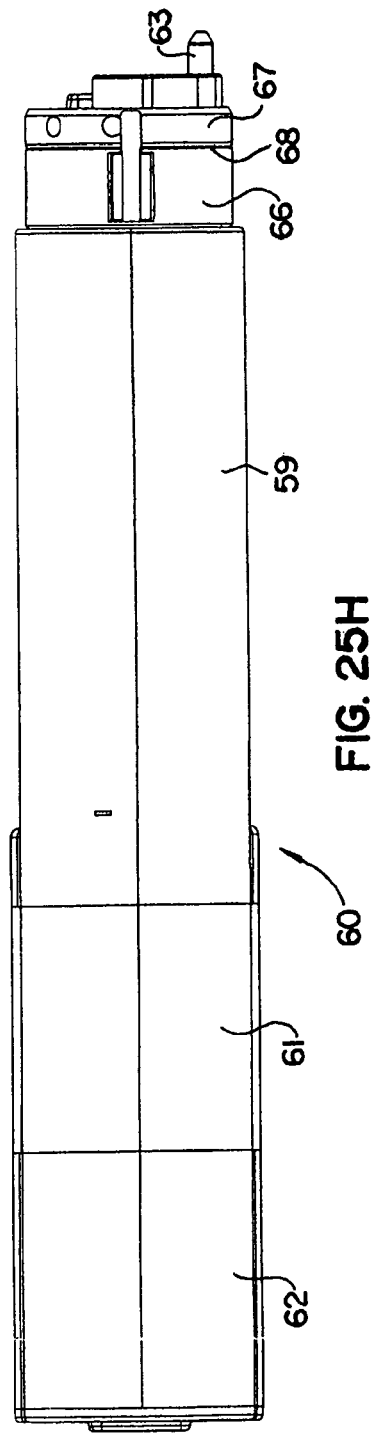
FIG. 25G
FIG. 25H

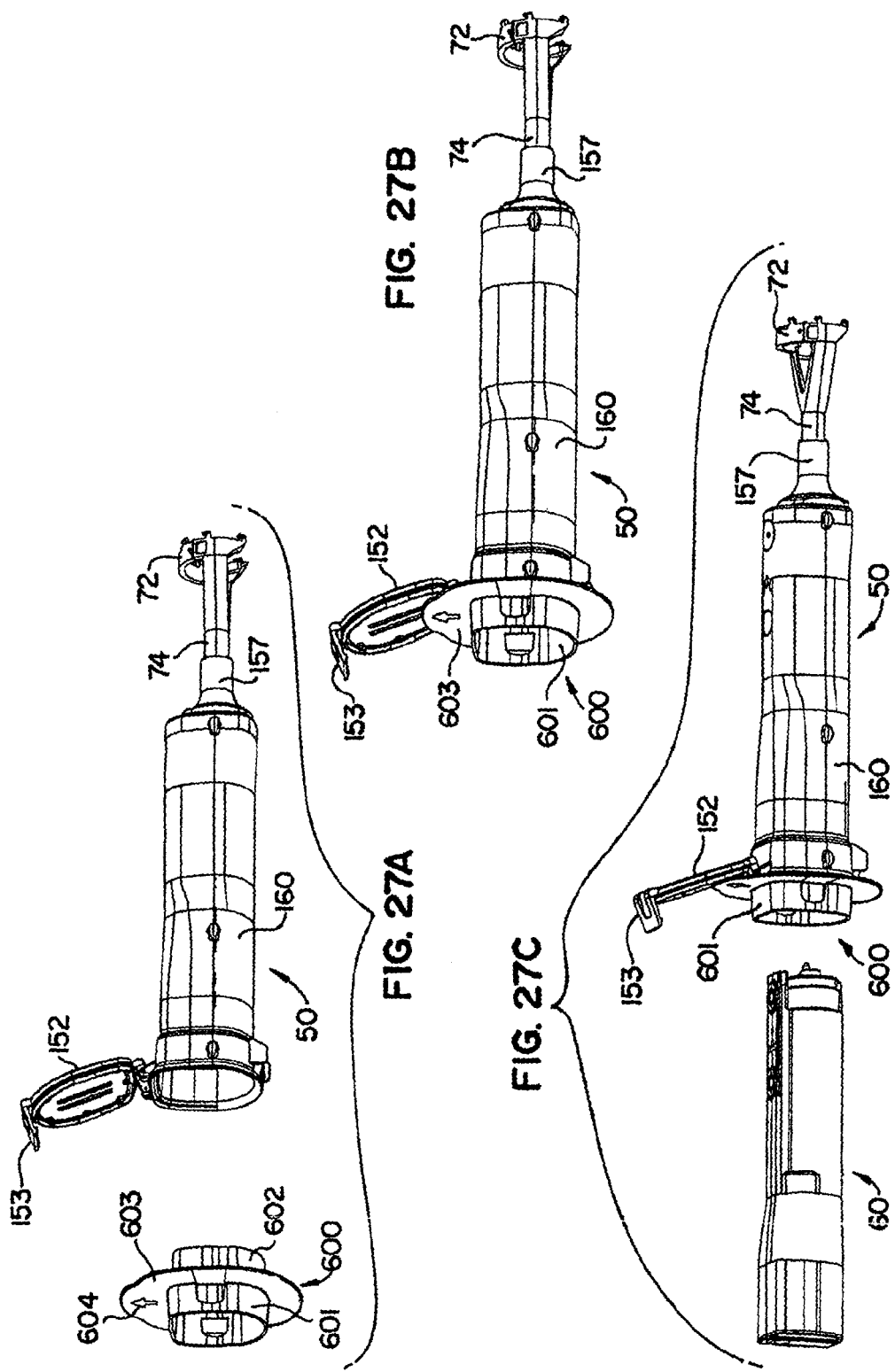

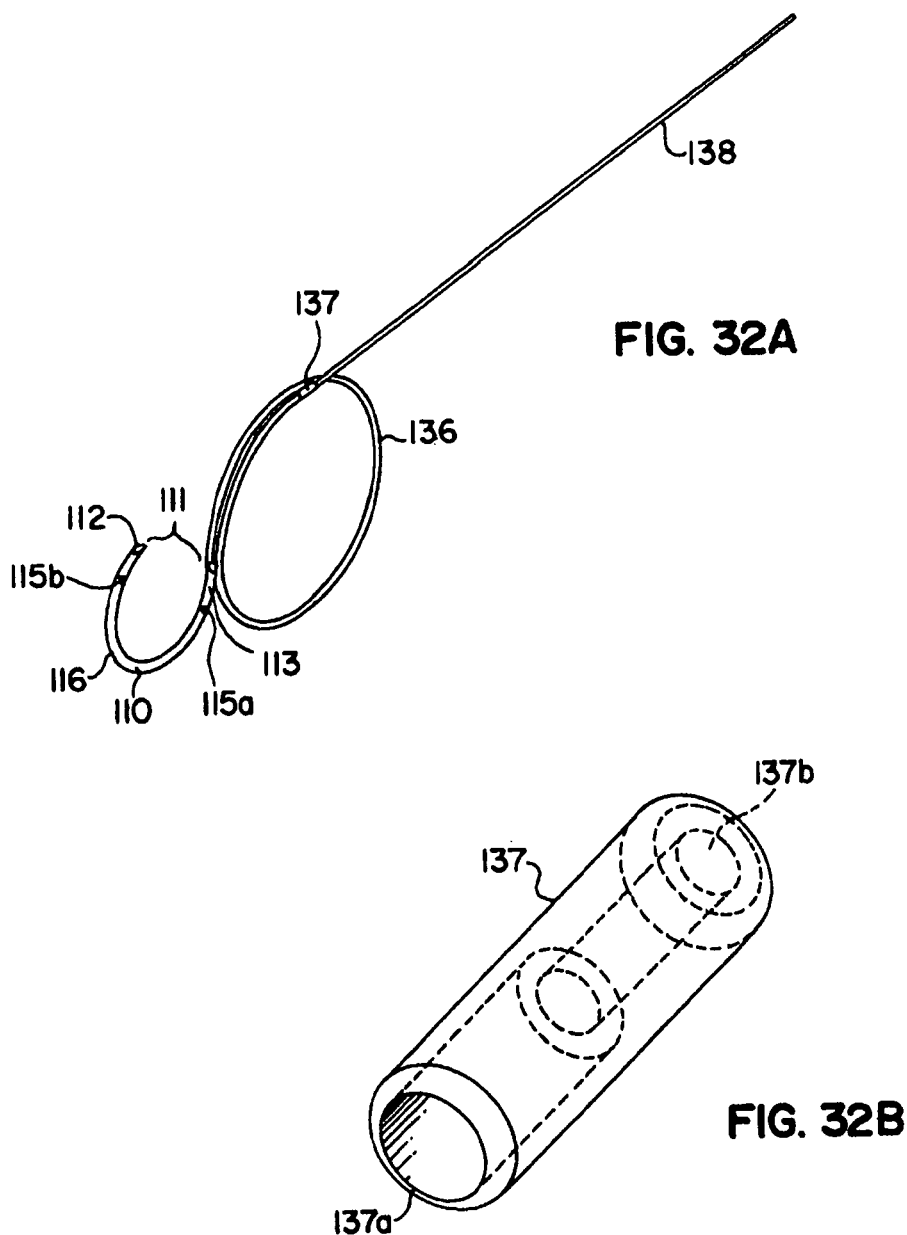

SUTURING NEEDLE

RELATED APPLICATIONS

This application is a Continuation of U.S. patent application Ser. No. 13/900,991 filed May 23, 2013, now abandoned, which is a Continuation of U.S. patent application Ser. No. 12/218,633 filed Jul. 17, 2008, now U.S. Pat. No. 8,469,973 which is a continuation of International Patent Application No. PCT/US2007/002204, filed Jan. 29, 2007 which claims the benefit of priority to U.S. Provisional Patent Application No. 60/763,038 filed Jan. 27, 2006. Each of the aforementioned patent applications is incorporated by reference herein in its entirety.

FIELD

The embodiments disclosed herein relate to a medical device for performing a procedure on tissue, such as bony tissue. Embodiments disclosed herein are appropriate for sternotomy closure, among other procedures. More particularly, embodiments disclosed herein are useful for the manipulation and control of a suture needle during sternotomy closure, and methods for using such a device.

BACKGROUND

Surgical procedures present many challenges which can compromise the health of the patient as well as the health of the medical professional. For some surgical procedures, such as cardiac surgery and pneumonectomy, access to the organ is generally gained by a sternotomy, a surgical procedure in which the sternum is divided with a device such as a saw or other suitable cutting instrument. After performing the sternotomy, the sternum must be re-approximated. The medical professional typically closes the sternum using a stainless steel needle with a sharp cutting point onto which is attached a suture comprising a length of relatively inflexible stainless steel wire, or alternatively, a combination of stiff stainless steel wire and flexible stainless steel cable. The wire (or combination cable and wire) suture is manually drawn through both sides of the sternum so that sufficient length of the wire is protruding from both sides of the sternum and there is no longer any slack wire below the sternum. After removing the needle from the wire, the medical professional must manually wrap an end of one wire around the other wire either with their hands or forceps, repeatedly twisting the two ends of the wires around each other in a helical or spiral manner. The medical professional then cuts the twisted wires to a desired length and uses surgical tools to bury the sharp, cut, twisted ends of the wires into the space between the re-approximated edges of the sternum so that the sharp, cut, twisted ends of the wire do not poke into the underside of the patient's skin. Typically, between six and eight wire sutures are placed in the sternum in order to close the sternum along its length.

The prior art sternotomy closure procedures present many problems to the medical professional and the patient. Manual suturing is often difficult because the suturing needle must be forced through tough, dense bone. Manual suturing also involves the handling and manipulation of a sharp suturing needle with an instrument such as a needle forceps, which can result in inadvertent, accidental needle pricks through a surgeon's or nurse's gloves, posing a potential risk of infection for the surgeon, nurse, staff, and patient. Manipulating an inflexible wire within the chest cavity underneath the sternum and ribcage is often difficult and awkward. For example, traditionally, the surgeon must manually lift the divided sternum upward when placing a suture through the bone, placing his or her hand in significant danger of needle puncture because of the force required to penetrate the bone. In addition, medical professionals are often stuck by the sharp, cut, twisted ends of the wires, and are thus subjected to the risk of potentially fatal bloodborne infections such as HIV/AIDS and Hepatitis B and C. Furthermore, the direct handling of the needle can cause the needle to become contaminated with pathogenic bacteria that can cause onset of infection at the site of the sutures. There is also a risk of the needle penetrating the heart and adjacent vessels and structures and causing a serious and often fatal infection.

Prior art sternotomy sutures for use by medical professionals are described, for example, in U.S. Pat. No. 4,074,732 entitled "Wire Cutting, Stripping and Twisting Tool;" U.S. Pat. No. 5,089,012 entitled "Surgical Suture, in Particular for Sternotomy Closure;" U.S. Pat. No. 5,318,566 entitled "Sternotomy Cable and Method;" and U.S. Pat. No. 5,830,234 entitled "Method for Double Wire Sternotomy Suture," all of which are hereby incorporated by reference herein in their entireties. Prior art sternotomy sutures require the medical professional to use their fingers or manual tools to manipulate the sutures and to provide an appropriate amount of tension to the sutures. In addition, U.S. Pat. No. 6,923,819 discloses an apparatus and method for surgical suturing with thread management, the entirety of which is hereby incorporated by reference herein.

Thus, it is evident that there is a need in the art for an apparatus and method for sternotomy closure that is safe, reliable, user friendly, and effective. The present invention provides a solution for this and other problems.

SUMMARY

The purpose and advantages of the present invention will be set forth in and become apparent from the description that follows. Additional advantages of the invention will be realized and attained by the methods and systems particularly pointed out in the written description and claims hereof, as well as from the appended drawings.

To achieve these and other advantages and in accordance with the purpose of the invention, as embodied herein, the invention includes an apparatus and method for joining tissue, such as bony tissue. According to aspects illustrated herein, there is provided a device for joining tissue that may be used, for example, for sternotomy re-approximation including a pusher assembly, and a cartridge. The pusher assembly has a drive arm extending from a drive shaft and a drive mechanism at a distal end of the drive arm. The drive mechanism is capable of releasably engaging and rotating a suturing needle having a pointed end and a blunt end about a rotational axis. The cartridge includes a protective housing and the suturing needle. The cartridge extends from a distal end of a cartridge holder assembly and is releasably attached to the cartridge holder assembly.

In accordance with a further aspect of the invention, a pointed end of the suturing needle is preferably positioned within the protective housing before and after a complete rotation of the suturing needle about the rotational axis. Moreover, if desired, a removable electronic module may be provided in the device that is controlled by an actuator that mechanically engages the drive shaft to rotate the drive shaft and the drive mechanism, thereby rotating the suturing needle about the rotational axis.

In accordance with a further aspect the invention also provides a cartridge for housing a suturing needle that can be used, if desire, for example, in sternum re-approximation. The cartridge includes a housing having a curved shape, an inner wall and an outer wall. The housing also includes a track in the inner wall of the housing whereby the suturing needle follows a curved path along the track during a revolution of the suturing needle. The cartridge further includes an aperture defined in the housing that intercepts the track, wherein the housing shields the pointed end of the suturing needle during at least a portion of the revolution of the suturing needle.

In accordance with another aspect, the invention further provides a suturing needle for use, for example, in sternum re-approximation. The needle includes a curved body having a pointed end that is protected at an end of a rotation cycle and a blunt end that engages a suturing material. The suturing material preferably includes a flexible leader engaged to a wire suture.

In accordance with still another aspect, the invention provides a method for joining tissue, such as sternum re-approximation. The method includes releasably engaging a cartridge having a protective housing and a suturing needle to a cartridge holder assembly of a tissue closure device. The method further includes, placing the tissue closure device having the cartridge and the suturing needle to cause an aperture in the cartridge to be disposed between a first side and a second side of a segment of tissue to be closed, such as a split sternum, wherein a pointed end of the suturing needle is positioned within the protective housing before and after a complete rotation of the suturing needle about a rotational axis. The method also includes activating an electronic module coupled to a pusher assembly that releasably engages the suturing needle to cause rotational movement of the suturing needle across the aperture in the cartridge and advance the suturing needle through the first side of the tissue segment and pulling a suturing material attached to the suturing needle through the first side of the tissue segment. The method further includes using the device to complete a stitch through the second side of the tissue segment.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the method and devices of the invention. Together with the description, the drawings serve to explain the principles of the invention.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 5B and FIG. 5C are sectional views of the tissue closure needle and the pusher assembly.

FIG. 22 shows an alternative design of the needle brace of FIG. 19, in which the stop at the pointed end of the needle comprises a flexible tab, which can aid in securing the brace onto the cartridge.

FIG. 23 shows the needle brace of FIG. 22 installed onto the cartridge, showing the flexible tab snapped onto the point of the needle.

FIGS. 27A-F show the installation of the funnel into the back end of the handle of the suturing device, with the funnel aligned with the barrel of the handle (A and D), the funnel in position within the handle (B and E), and the electronic module of FIG. 24 aligned with the installed funnel (C and F).

FIG. 32A shows an embodiment of a tissue closure needle having the tissue closing suture material attached thereto. FIG. 32B shows an expanded view of a crimp that houses the ends of the two materials that form a tissue closure suture material.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Reference will now be made in detail to the present preferred embodiments of the invention, examples of which are illustrated in the accompanying drawings. The method and corresponding steps of the invention will be described in conjunction with the detailed description of the system.

The devices and methods presented herein may be used for tissue closure. The present invention is particularly well suited for procedures involving bony tissue, such as sternotomy closures. As depicted, the disclosed tissue closure device, or suturing device, is a motorized, electrically powered apparatus. The power source can be battery or standard wall electrical power. The tissue closure devices disclosed herein advantageously prevent accidental needle punctures to the medical professional and readily and easily drive needles through bony tissue, eliminating the need to manually force the needles through the bone. Within the context of sternotomy closure, the disclosed devices protect the heart and adjacent vessels and structures from inadvertent needle punctures during closure and replicates the standard sternotomy closure technique. In so doing, the disclosed embodiments provide easier and more fluent manipulation of the wire or wire/cable combination within the chest cavity or other anatomy, and produce tissue closure in a time efficient manner so the patient is not subjected to health risks associated with having a tissue segment, such as the sternum, open for more time than necessary.

Figure 1:
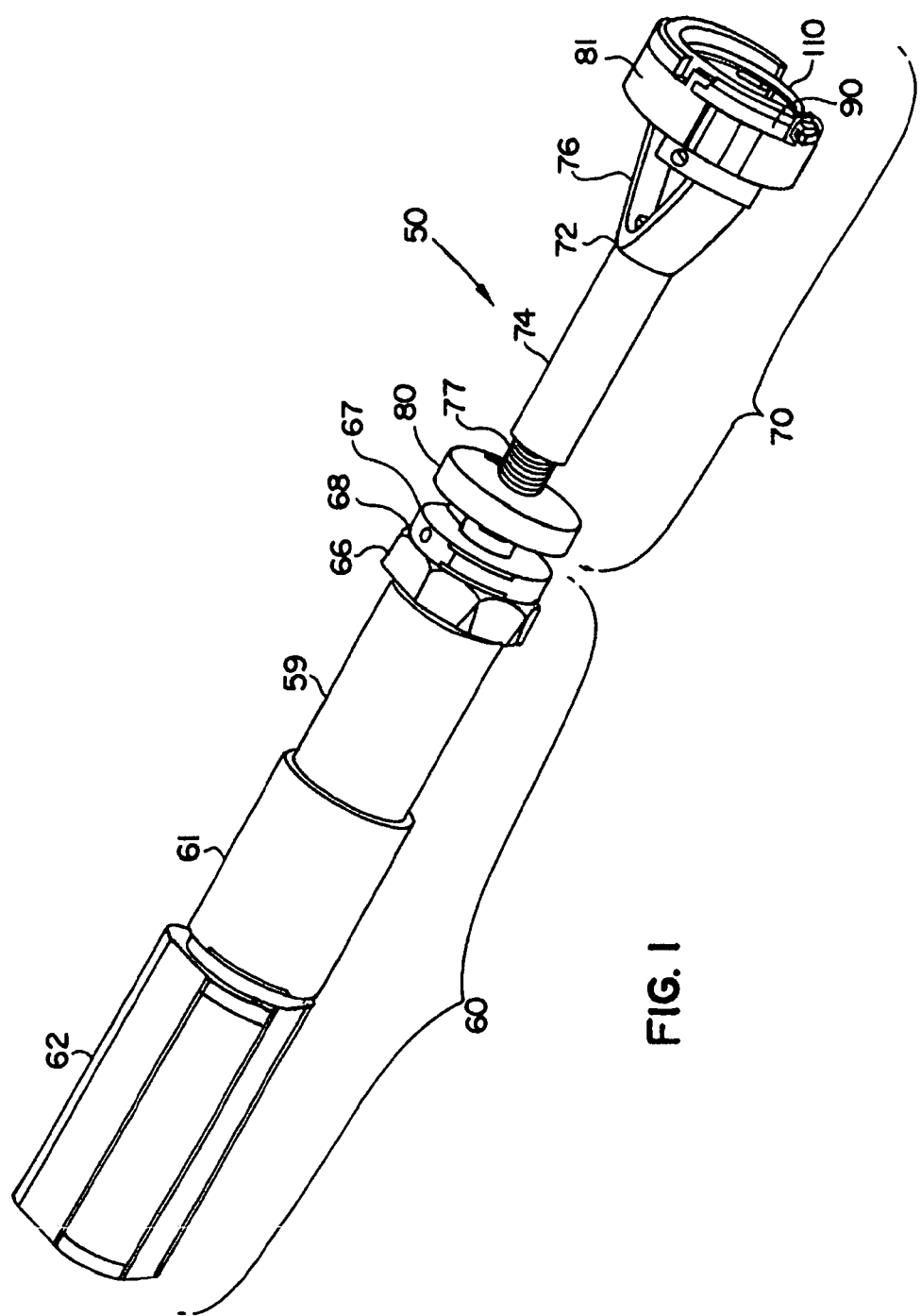
FIG. 1 is a pictorial view of the main components of a tissue closure device provided in accordance with the invention.

The main components of a tissue closure device of the presently disclosed embodiments are shown generally at 50 in FIG. 1. The tissue closure device 50 can be used to produce a continuous, or more commonly, an interrupted suture so as to enable closure of the sternal halves after a sternotomy procedure, for example. As depicted, device 50 is a motorized, battery-powered apparatus designed to prevent needle punctures during sternotomy closure or other similar procedures. Device 50 delivers reliable closure using standard needles and wires and replicates standard tissue (e.g., sternotomy) closure techniques. Device 50 easily drives needles through bone as well as other tissue, thus eliminating the need to manually force the needles through the bone; and protects the heart and adjacent vessels and structures from inadvertent needle punctures during closure.

Referring to FIG. 1, the tissue closure device 50 includes a removable electronic module 60 including a battery pack 62, an electric motor 61, and a gear box 59, as well as electronic circuits. The gear box 59 further includes a shaft that runs through a stop plate 66, a bearing surface 68, and a drive wheel 67. A drive pin 63 engages the drive wheel 67 and when in use, mates with a hole in a drive plate 80 that is part of a front end assembly 70. The bearing surface 68 acts as a lubricating surface between the stop plate 66 and the drive wheel 67. The bearing surface 68 may be any lubricious material having a low coefficient of friction, for example fluoropolymer compounds such as those including polytetrafluoroethylene (PTFE).

The electric motor 61 preferably is compact yet powerful. In one embodiment, a DC motor can be selected from the Maxon RE-max 29 series, for example, commercially available from Maxon Precision Motors, Inc. of Fall River, Mass. Model no. 226784 can be used, which weighs 159 grams, is 29 mm in size, operates on 9 volts, can generate 22 watts, and has a no-load speed rating of 7630 RPM. The gear box 59 can be selected from, for example, the Maxon Gearhead GP32C series, which is 32 mm is size. Model no. 166943 can be used, which has 3 stages, weighs 194 grams, and has a 103:1 gear reduction ratio.

As depicted, the front end assembly 70 includes a pusher assembly (not visible) and a cartridge holder assembly 72. The pusher assembly has a drive arm that houses a drive mechanism ("pawl") and a drive shaft that runs throughout the length of the front end assembly 70 and enters the drive plate 80. A needle cartridge 90 carrying a tissue closure needle 110 may be removably attached to a distal end 81 of the cartridge holder assembly 72.

Figure 2A:
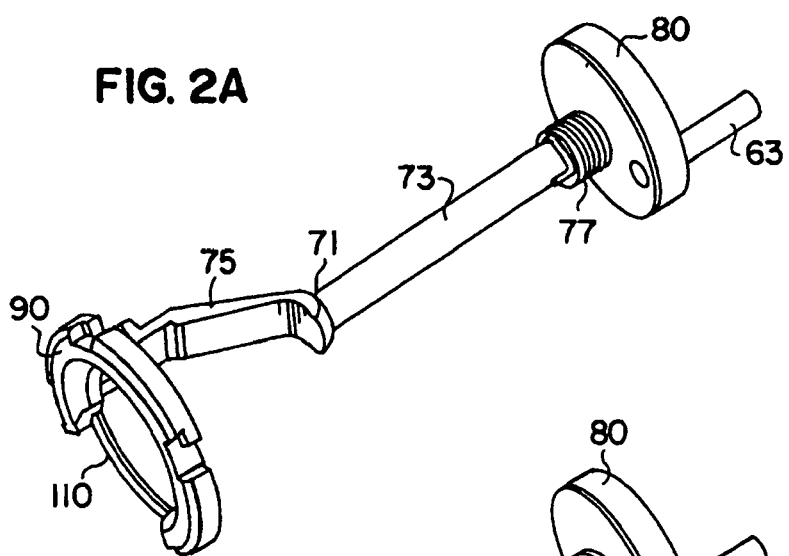
FIG. 2A and FIG. 2B are perspective views of a front end assembly of the tissue closure device of FIG. 1.
Figure 2B:
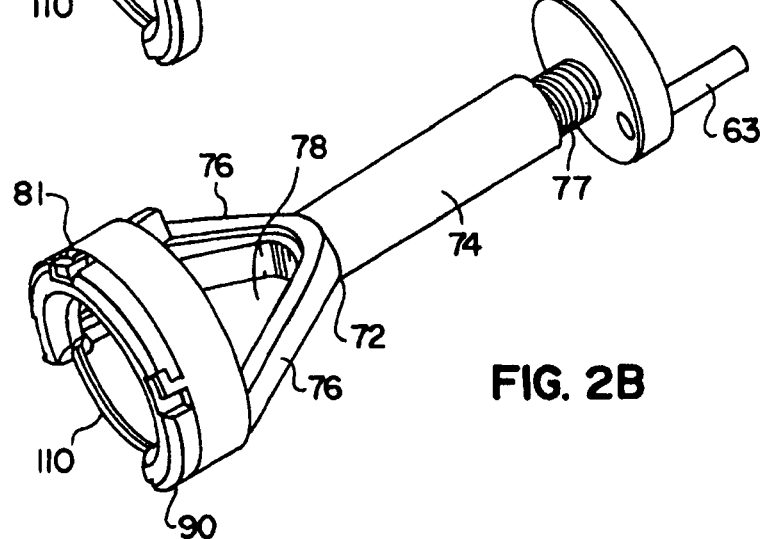

FIG. 2A and FIG. 2B show the front end assembly 70 including a pusher assembly 71 and the cartridge holder assembly 72 with the attached disposable needle cartridge 90 which houses the tissue closure needle 110. The pusher assembly 71 includes a drive shaft 73 and a drive arm 75 that is in intimate contact with the needle 110 via a pawl. The drive shaft 73 engages a spline in the drive plate 80 so the drive shaft 73 is rotationally attached to the drive plate 80. When the electronic module is attached to the front end assembly the drive shaft 73 engages a bushing located in the drive wheel 67. The cartridge holder assembly 72 (shown in FIG. 2B) includes a shaft barrel 74 and a support arm assembly 76 that is comprised of a pair of "skeletalized" arms extending along mutually divergent axes so as to provide an opening 78 to view the device 50 during its operation. The open configuration of the support arms 76 are minimal in bulk and provide a relatively wide opening 78 that allows the medical professional to directly view the aperture in the needle cartridge 90 and cartridge holder assembly 72, the space, for example, between a first side and a second side of a split sternum and needle advancement through the space during operation of the tissue closure device 50. Although the embodiment shown in FIG. 2 has a plurality of support arms 76, other variants include a support arm assembly comprising a single support arm. The improved viewing ability offered by the shape and configuration of the support arm assembly 76 enables precise device placement over the sternum in the case of a sternotomy closure procedure, and uniform advancement of the tissue closure device 50 after every stitch to provide a uniform and symmetric suture, thereby protecting the heart and adjacent vessels and structures from inadvertent needle punctures during closure.

The distal end 81 of the cartridge holder assembly 72 is where the needle cartridge 90 is disposably attached. The needle cartridge 90 comprises a circular housing that may be formed of a suitable rigid medical grade sterilizable metal or plastic material. Preferably, the material forming the cartridge 90 possesses both rigidity and a low coefficient of friction to reduce the power required to move the needle disposed within it. One such material, for example, is Lubricomp DFP22H, produced by GE Plastics, a polycarbonate containing 10% glass fill, 8% PTFE (Teflon), and 2% silicone. Constructing the cartridge from this material can provide for up to 20% more driving power at the point of the needle. The housing may be releasably retained by the distal end 81 of the cartridge holder assembly 72 by known means, such as a plurality of grooves located along on the edge of an inner lip in diametrically opposite positions that are capable of engaging the same plurality of slots correspondingly located in the distal end 81 of the cartridge holder assembly 72. The grooves when engaged enable the needle cartridge 90 to be retained by the distal end 81 of the cartridge holder assembly 72. A torsion return spring 77 engages the shaft barrel 74 and the drive plate 80 and is responsible for returning the drive shaft 73 back to a "start" position such that when the electronic module 60 is attached to the front end assembly 70 the drive pin 63 will properly engage the drive plate 80 of the front end assembly 70.

Figure 31A:
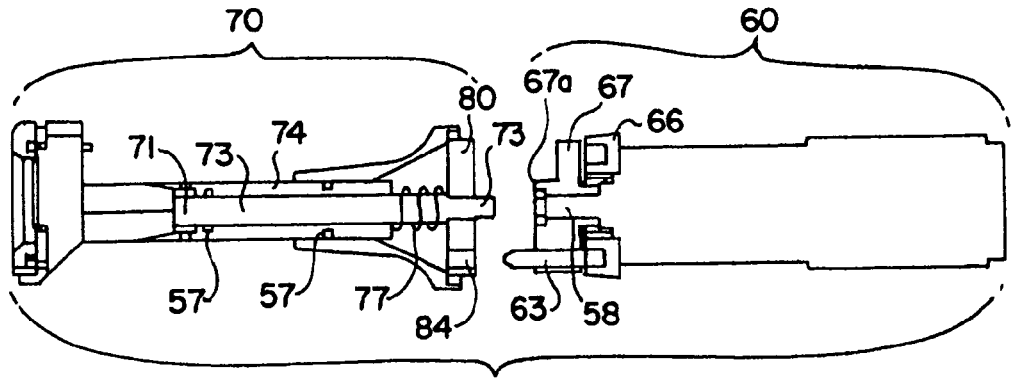
FIG. 31A, FIG. 31B, and FIG. 31C show segmented sectional views of the main components of the tissue closure device.
Figure 31B:
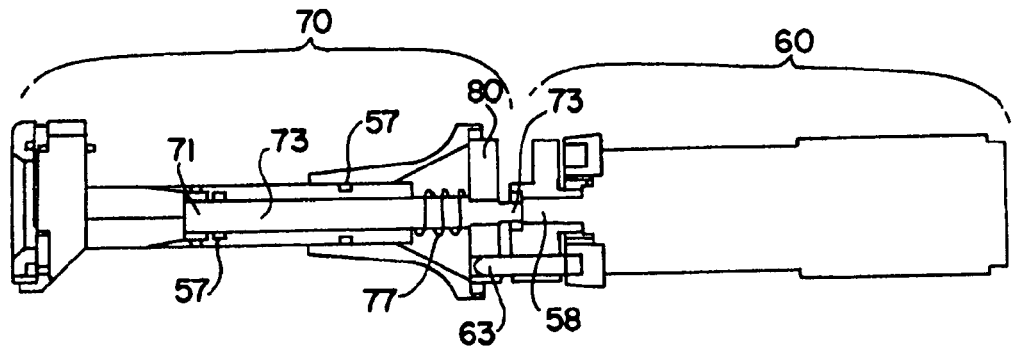
Figure 31C:
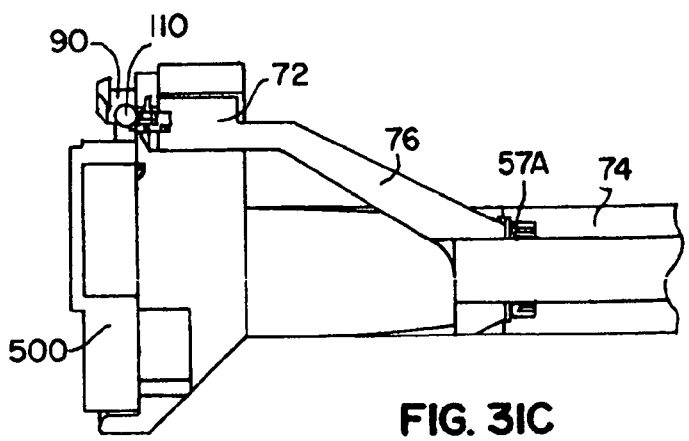

As best shown in FIG. 31A and FIG. 31B, O-rings 57 between the pusher assembly 71 and the cartridge holder assembly 72 create a separation barrier to ensure the device 50 stays sterile during operation. The first O-ring 57 seals the rotating shaft against the front end assembly. The second O-ring 57 seals closer to the housing and seals the front end assembly against the nose collar 157. The plurality of O-rings 57 provide a sterile barrier to seal the device exterior from the interior of the handle. Alternatively, as shown in FIG. 31C, a Teflon seal 57A can be used, which provides for a more durable barrier to the entry and exit of fluids and other possible contaminants. The barrier seal eliminates means of exiting of any non-sterile germs, debris, particles, etc., from the inside of the device to the sterile outside of the device front end.

Figure 3A:
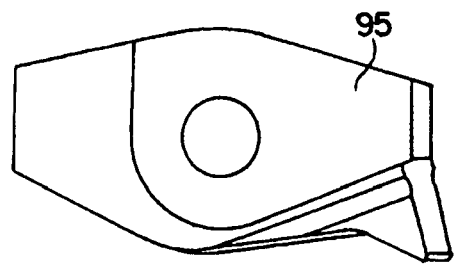
FIG. 3A shows an expanded view of a pawl.
Figure 3B:
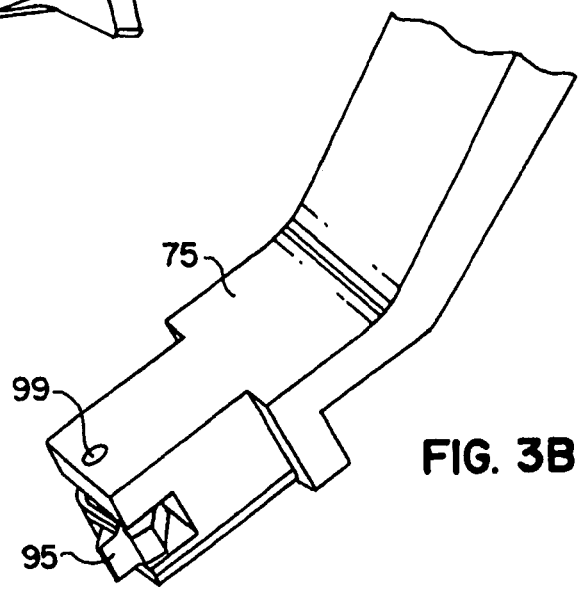
FIG. 3B and FIG. 3C show an expanded view of a pusher assembly with the pawl in place.
Figure 3C:
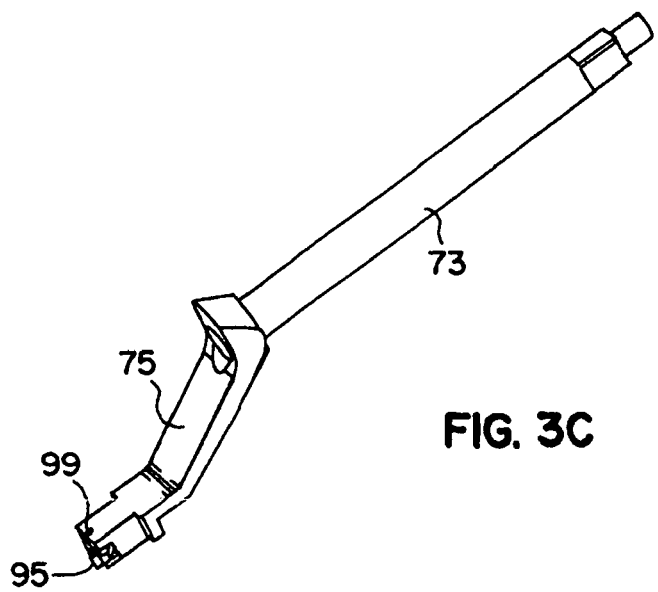

FIG. 3B and FIG. 3C show expanded views of the pusher assembly including a pawl 95 (as shown in FIG. 3A) located at the tip, which resides in a slot in the drive arm 75 of the pusher assembly, and is connected to the drive arm 75 by a pivot pin 99. The needle (not shown) is driven in a circular path by the pawl 95.

Figure 4:
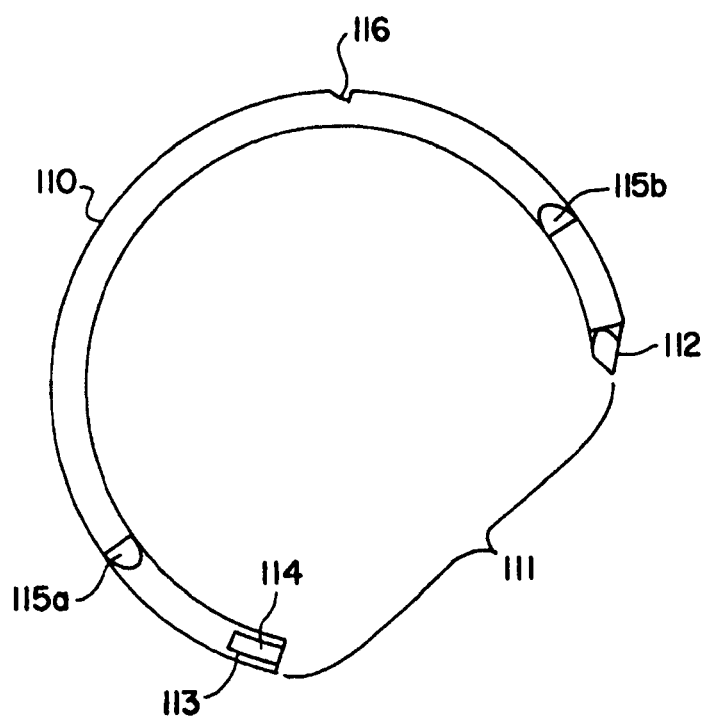
FIG. 4 shows an expanded view of a curved tissue closure needle.

FIG. 4 shows an embodiment of the curved tissue closure needle 110 of the presently disclosed embodiments, which is particularly suitable for penetration through bony material. The needle 110 is formed as a circular split ring defining an aperture (or gap) 111, a sharp, pointed end 112 and an opposite blunt end 113. A cylindrical bore 114 aligned axially with respect to the needle 110, is located at the blunt end 113. The leading end of the suturing material for tissue closure is inserted into the bore 114 and restrained by mechanically crimping. Alternatively, the opening for accommodating the suture material can be in the form of an "eye" wherein the leading end of the suturing material may be passed through for attaching it to the needle 110. To enable the needle 110 to penetrate to the required depth, the needle 110 preferably has an arcuate extent between about 250° and about 330°.

The needle 110 further includes two symmetric notches 115a and 115b along the radially rear edge, i.e. the edge proximal to the cartridge holder assembly. The notch 115b is positioned toward the sharp pointed end 112 of the needle 110. The notch 115a is positioned toward the blunt end 113 of the needle 110. The notches 115a and 115b are located opposite to one another, each having a perpendicular (about 90°) segment and an angular segment that makes an angle of about 60° with the perpendicular segment. The notches 115a and 115b are engaged by the drive mechanism (pawl) in the cartridge holder assembly 72 and enable the needle 110 to undergo a rotational movement upon actuation of the drive mechanism, thereby causing it to penetrate and advance through the space spanning the tissue segment, such as a split sternum. A notch 116 is located on the radially outer edge ("outer notch") of the needle 110 proximally to the notch 115b that is closer to the sharp, pointed end 112. The outer notch 116 engages with an anti-rotate bar located in the cartridge holder assembly 72, whereby rotation of the needle 110 in a direction opposite to the advancing direction or "needle backing-up" is prevented. The positive engagement of the needle outer notch 116 during operation prevents the needle 110 from straying out of sequence during the suturing process.

The needle 110 is enclosed within a cartridge, so the sharp pointed end 112 is not exposed. This needle position, as loaded, is referred to as the "home" position. In the home position, the needle 110 is fully contained within the cartridge housing to eliminate needle-pricks during handling of the cartridge or the loaded device. The width of the aperture in the needle cartridge is comparable to and corresponds with the width of the gap in the needle 110 so that when the needle 110 is in the home position the needle 110 does not project materially into the aperture 111. Such an alignment causes the needle 110 to reside entirely within the needle cartridge, thereby preventing inadvertent contact of the sharp pointed end 112 with the user's fingers during handling of the disposable needle cartridge for placement on the cartridge holder assembly or disposal after use, and while operating the tissue closure device 50. Such protection of the needle 110 in the tissue closure device 50 prevents accidental "needle-pricks" from occurring, thereby substantially reducing the risk of infection caused by pathogenic bacteria or viruses that may contaminate the needle 110 during or after use prior to disposal. The needle 110 may be rotated in a curved track of the needle cartridge about the longitudinal axis of the suturing device 50 to advance the pointed needle end 112 so that the needle 110 first spans the aperture 111 and then returns to the home position. The suturing material is attached to the needle 110, and therefore follows the path of the needle 110. The suturing material may then be cut and twist tied and secured by an appropriate method. Every stitch, whether a single, interrupted stitch, or one of a series of continuous, running stitches may be placed in like manner. The tissue closure, or suturing device 50, therefore, may be used to insert either a single stitch, or to insert a suture comprising a plurality of continuous stitches as a replacement method for a more tedious and time-consuming manual suturing process.

Figure 5A:
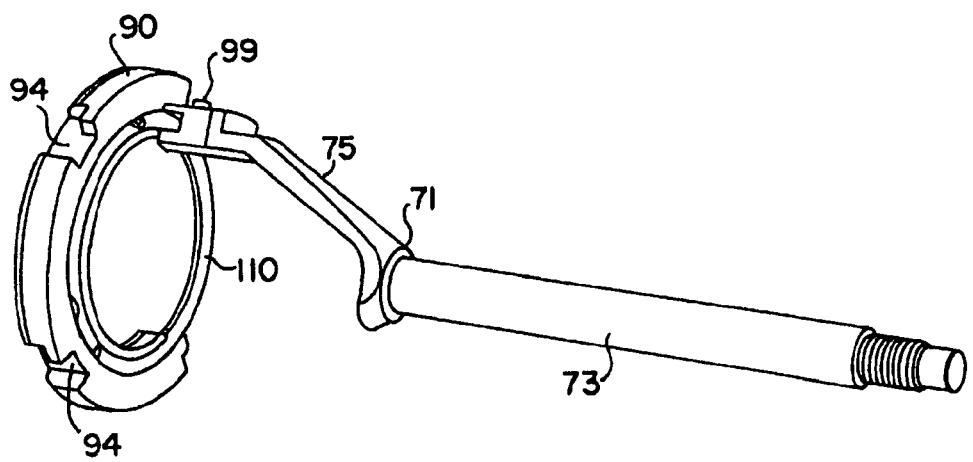
FIG. 5A is a perspective view of the relative configuration of a tissue closure needle with respect to the pusher assembly.

FIG. 5A provides a detailed view of the pusher assembly 71 with relation to the suturing needle 110. The pawl at the tip of the drive arm 75 is capable of interfitting with wedge shaped notches located along the radially inner edge of the needle 110. The drive arm 75 is capable of sweeping back and forth in an arc spanning about 190°. The drive arm rotates more than 180°, and the overdrive accounts for any design irregularities and tolerances on the needle 110 and the moving parts and ensures that the pawl will always pick up the needle notch 116.

The advancing movement of the needle 110 during operation causes triangular slots along the radially inner edge of the needle 110 to align with the wedge-shaped pawl in the drive arm 75, thereby causing the pawl to engage the slots due to a positive pressure exerted on the pin 99, and to "lock" into the slots. The rotatory advancing movement of the needle 110 is therefore controlled to occur sequentially through about 190° each time the tissue closure device 50 is actuated. For each suture stitch, the needle 110 rotates through an arc of about 360°, while the drive arm 75 rotates back and forth for a total of about 760° degrees per stitch.

FIG. 5B and FIG. 5C are sectional views of the tissue closure needle and the pusher assembly. As shown in FIG. 5B, a flat spring 96 asserts tension on the pawl 95 to push the pawl 95 distally into the needle 110 and into the notch 115b. When the pawl 95 is rotated, the pawl 95 picks up that notch 115b and drives the needle 110.

FIG. 5C shows the pawl 95 not engaged in the notch 115b and engaging the surface of the needle 110. As the pawl 95 moves along the outer surface of the needle 110, the pawl 95 encounters the notch 115b. The pawl tip engages the ramp for the notch 115b and the flat spring 96 pushes the pawl 95 into the needle notch 115b.

FIG. 5C shows a pawl stop 98 that permits the pawl tip to only extend a certain amount into the needle 110 to not bind the needle 110 and cause the needle 110 to stop. The pawl 95 has an angled surface that angles away from the pawl stop 98. When the pawl 95 rotates clockwise, the pawl 95 can only turn until the angled surface contacts the pawl stop 98. The pawl 95 contacting the pawl stop 98 is shown in FIG. 5B. The pawl stop 98 prevents further rotation of the pawl 95 and prevents the pawl 95 from binding the needle 110 in the cartridge 90.

Figure 6:
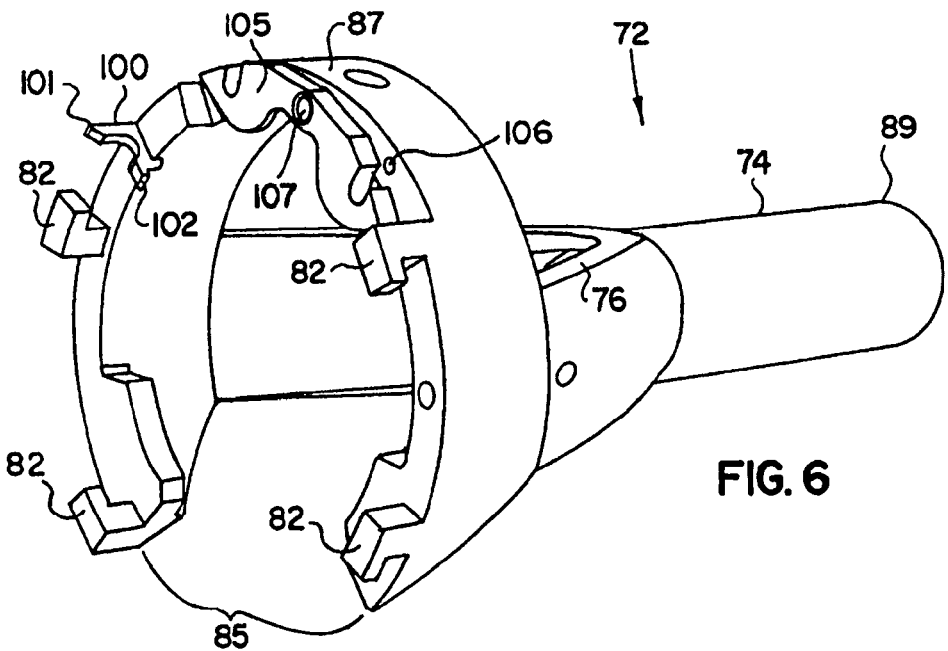
FIG. 6 is a perspective view of a cartridge holder assembly of the tissue closure device of FIG. 1.

FIG. 6 shows a close-up view of the distal end 81 of the cartridge holder assembly 72. The cartridge holder assembly 72 is composed of a sterilizable medical grade material which can either be a metallic material such as stainless steel to enable its reuse subsequent to sterilization following a prior use, or a sterilizable medical grade plastic material, in which case, it may be discarded and disposed after a single use. The cartridge holder assembly 72 has a cylindrical configuration with a distal edge 87 and a proximal edge 89 with respect to the device actuator handle (not shown), with an aperture 85 that corresponds in dimension and location to coincide with a substantially similar aperture located in the disposable needle cartridge. The cartridge holder assembly 72 additionally comprises a plurality of slots 82 located along on the distal edge 87 that are located opposite to one another, and are capable of engaging the same plurality of retaining clips correspondingly located in the needle cartridge housing (not shown). The cartridge holder assembly 72 further comprises a cylindrical slot (not visible) located on the distal edge 87 that is capable of engaging a pivoting pin of identical diameter correspondingly located on a gate assembly 105. The proximal edge 89 of the cartridge holder assembly 72 is attached to the shaft segment 74 by the support arm assembly 76. The gate assembly 105 prevents the needle from leaving the track and falling out into the back of the cartridge holder assembly 72. The gate assembly 105 pivots on a pivot pin 107 like a rocker switch during each actuation of the tissue closure device 50 to permit a circular movement of the drive mechanism that engages the needle. Stop pins 106 located on the cartridge holder assembly cause the gate assembly 105 to stop and reverse direction, like a "see-saw," "up-down" motion. The gate assembly 105 precludes the lateral movement and dislocation of the needle within the cartridge holder assembly 72. The gate assembly 105 is able to pivot on the pivot pin 107 so that the drive arm 75 which engages with the needle via the pawl can pass by the gate assembly 105. An anti-rotate bar 100 is capable of engaging with the needle cartridge 90 to lock it in place on the cartridge holder assembly 72 as well as to engage the needle, whereby rotation of the needle in a direction opposite to the advancing direction or "needle backing-up" is prevented.

Figure 7:
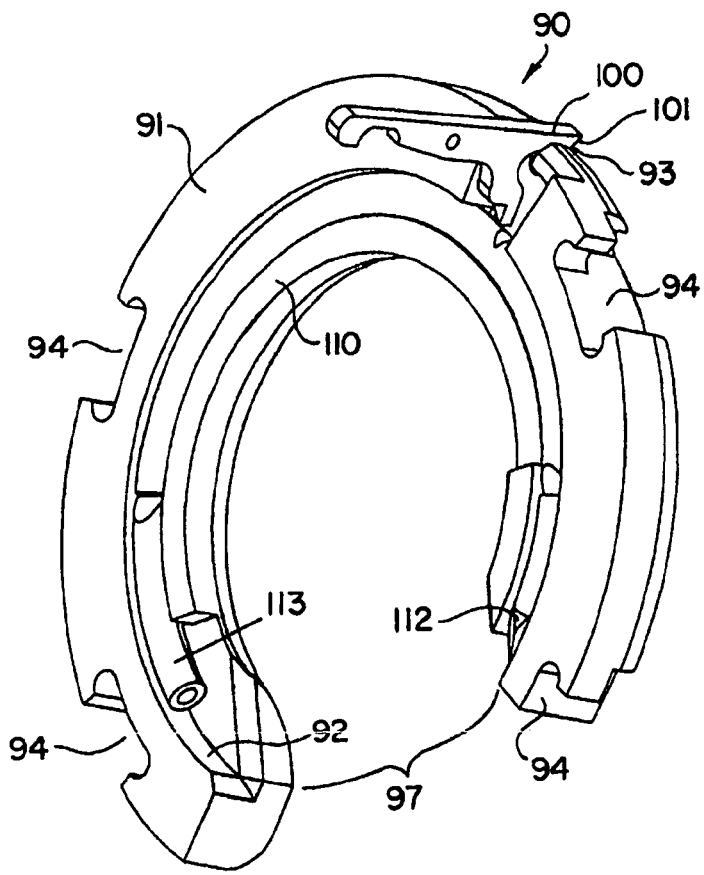
FIG. 7 shows an expanded view of a needle cartridge.

FIG. 7 shows a close-up view of a disposable needle cartridge 90 of the presently disclosed embodiments, which is preferably offered in a sterilized sealed package. The needle cartridge 90 comprises a circular housing 91 that may be formed of a suitable rigid medical grade sterilizable metal or plastic material. The material forming the cartridge 90 preferably has both rigidity and a low coefficient of friction to reduce the power required to move the needle disposed within it. One such material, for example, is Lubricomp DFP22H, produced by GE Plastics, a polycarbonate containing 10% glass fill, 8% PTFE (Teflon), and 2% silicone. Constructing the cartridge from this material can provide for up to 20% more needle driving power at the point of the needle. The housing 91 may be releasably retained by the cartridge holder assembly at the distal end of suturing device 50 by known means, such as a plurality of grooves 94 in diametrically opposite positions that are capable of engaging with the plurality of slots on the distal edge of the cartridge holder assembly. The needle cartridge 90 further comprises a groove 93 that is capable of engaging the anti-rotate and locking bar 100 correspondingly located on the cartridge holder assembly.

While the grooves 94 when engaged enable the needle cartridge 90 to be retained by the cartridge holder assembly, the groove 93 when engaged with the anti-rotate and locking bar 100 causes an aperture 97 defined in the needle cartridge 90 to be aligned with the corresponding aperture in the cartridge holder assembly. The needle cartridge 90 further comprises a circular groove or "track" 92 that is inscribed in the inside surface of the housing 91, which lies in a plane that is perpendicular to the longitudinal axis of both the housing 91 and that of the suturing device 50. The aperture 97 interrupts the track 92.

The arcuate suturing needle 110 composed of medical grade stainless steel or similar material is slidably positioned in the track 92. The radius of the arc defining the arcuate needle 110 is approximately equal to the circumference to the needle cartridge 90 at the aperture 97 therein. The needle 110 normally resides in a "home" position in the track 92 such that the gap in the arcuate needle 110 is in alignment with the aperture 97 in the cartridge 90. The sharp, pointed end of the needle 110 is situated on one side and entirely within the confines of the housing aperture 97; the pointed end of the needle 110 is, therefore, shielded by the cartridge housing 91. The blunt end of the needle 110 that is attached to a suturing material is located at the opposite side of the aperture 97. The sharp, pointed end of the needle 110 is, therefore, wholly contained within the cartridge 90 and does not protrude beyond the housing of the cartridge 90. Thus, the sharp pointed end of the needle 110 is not exposed to the user.

Figure 8A:
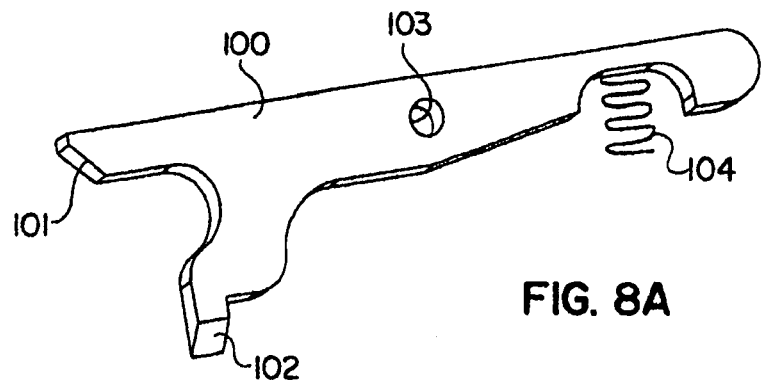
FIG. 8A shows an expanded view of an anti-rotate and locking bar.
Figure 8B:
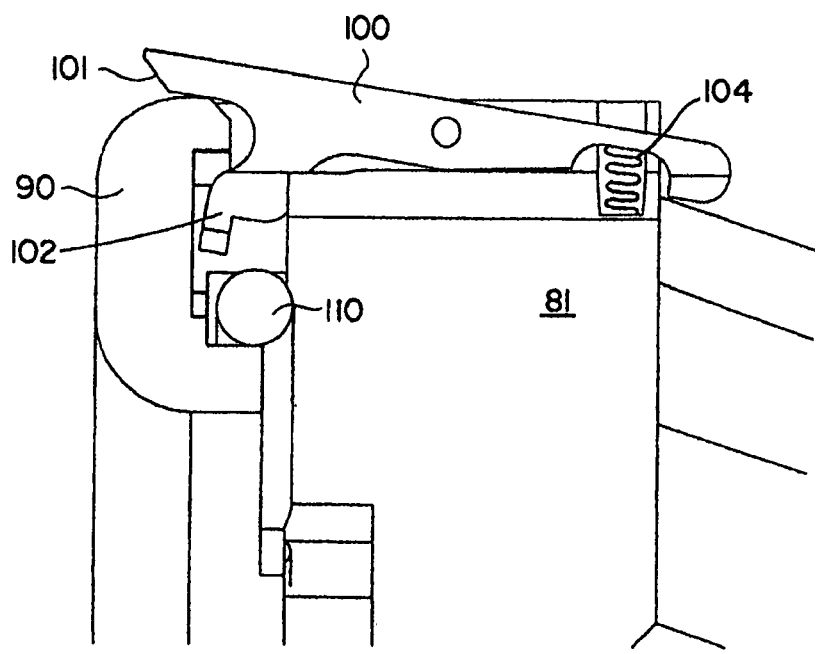
FIG. 8B shows an expanded view of the relative configuration of the anti-rotate and locking bar with respect to a suturing needle housed in a needle cartridge.

FIG. 8A shows a close-up view of the anti-rotate and locking bar 100. As shown in FIG. 8B, the anti-rotate and locking bar 100 includes a cartridge locking surface 101, which makes contact with the needle cartridge 90 and locks it into place, and an anti-rotate surface 102, which contacts the needle 110. A coil spring 104 engages the cartridge holder assembly 72 and allows the anti-rotate and locking bar 100 to move up and down so as to lock or un-lock the needle cartridge 90 into place on the cartridge holder assembly 72.

Figure 14A:
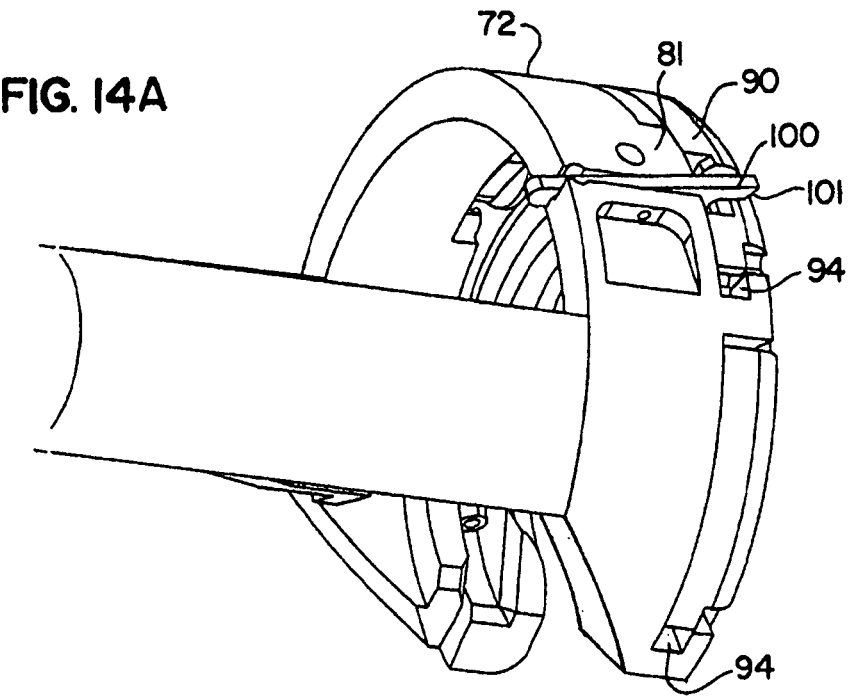
FIG. 14A shows a perspective view of the relative configuration of the needle cartridge with respect to the cartridge holder assembly and the anti-rotate and locking bar before the needle cartridge has been locked into place.
Figure 14B:
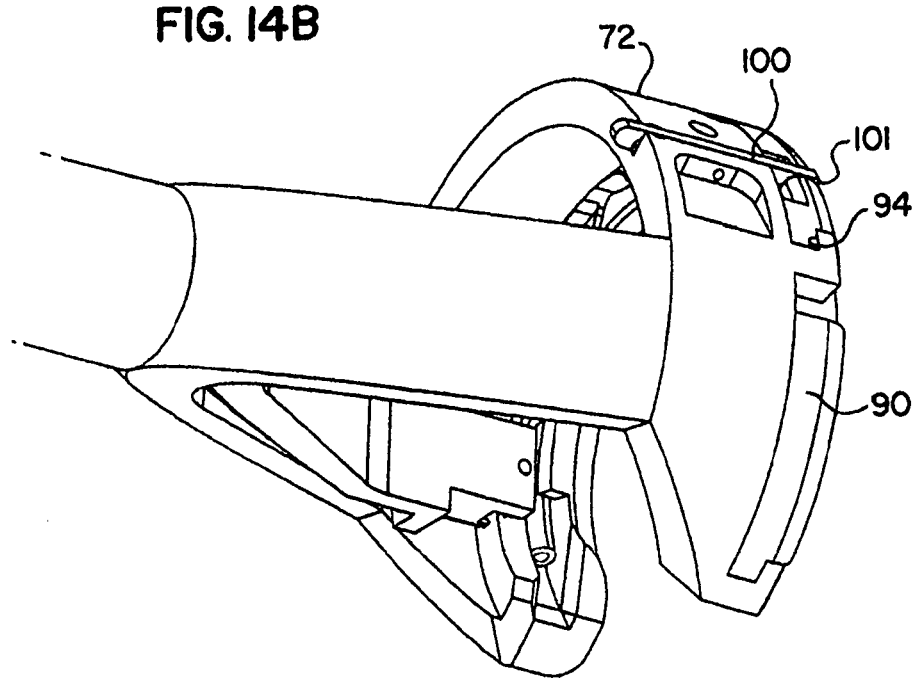
FIG. 14B shows a perspective view of the relative configuration of the needle cartridge with respect to the cartridge holder assembly and the anti-rotate and locking bar after the needle cartridge has been locked into place.

FIGS. 14A and 14B show an enlarged view of the distal end 81 of the cartridge holder assembly 72. In FIG. 14A, the needle cartridge 90 is in a non-locked position. In order to lock the needle cartridge 90, the needle cartridge 90 needs to be rotated counter clockwise. To unlock the needle cartridge 90 from the distal end 81 of the cartridge holder assembly 72, the anti-rotate and locking bar 100 may be pressed down to engage the coil spring and this will allow the anti-rotate and locking bar 100 to pivot at pivot pin 103.

Figure 9:
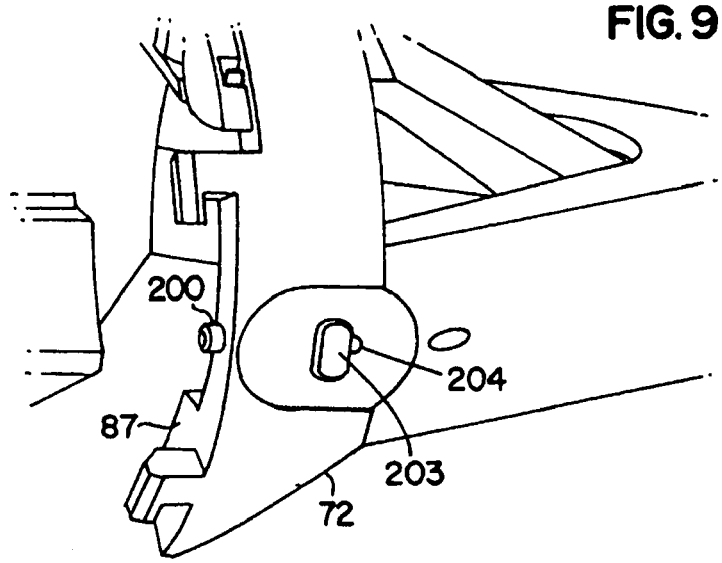
FIG. 9 shows close-up view of an alternative cartridge locking mechanism utilizing a retractable pin incorporated into the cartridge holder assembly instead of a locking bar.
Figure 10:
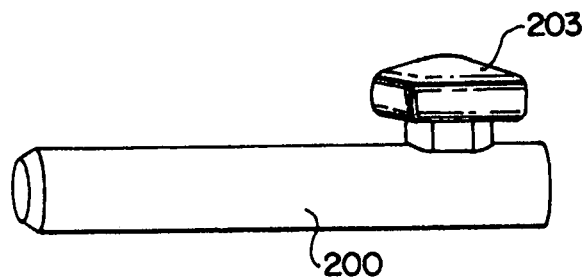
FIG. 10 shows an isolated view of the cartridge locking pin of FIG. 9.
Figure 11:
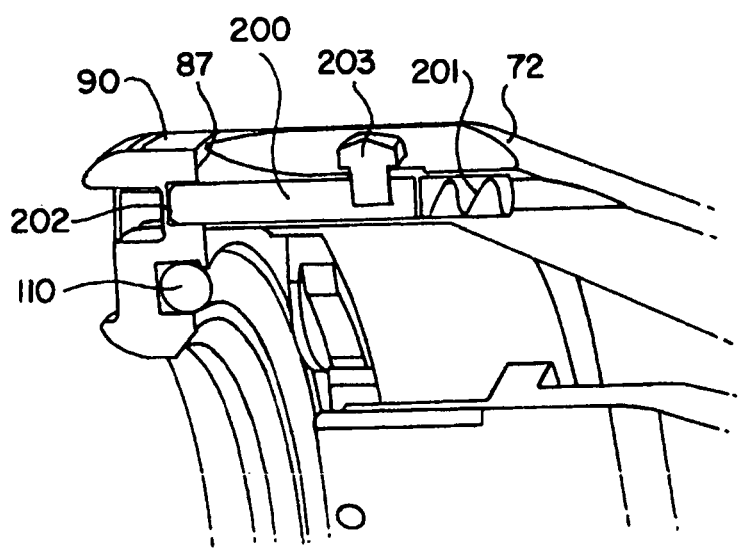
FIG. 11 shows a cutaway view of the cartridge locking pin of FIG. 9 engaged with the locking pin recess of the cartridge.
Figure 12:
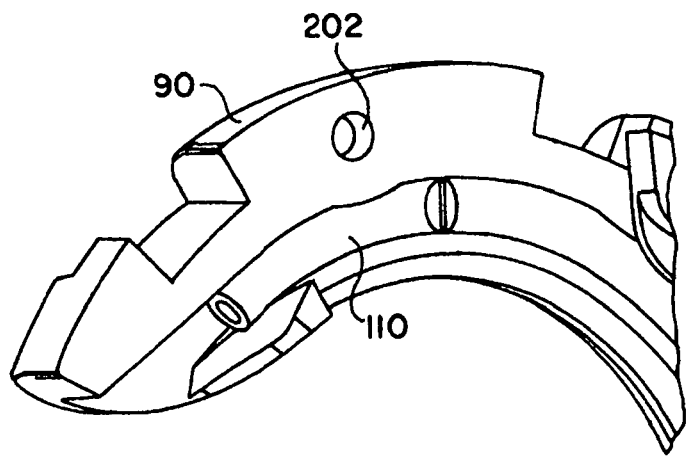
FIG. 12 shows the locking pin recess of FIG. 11 on the proximal surface of the needle cartridge.

FIG. 9 shows an alternative cartridge locking mechanism. A locking pin 200 is slidably disposed within the cartridge holder assembly 72. A handle and button 203 connected to the locking pin 200 allows the operator to slide the pin 200 proximally along the slot 204 from a position that protrudes from the distal edge 87 of the cartridge holder assembly 72 to a fully retracted position (not shown). As shown in the cross-sectional view of FIG. 11, the locking pin 200 is biased to protrude from the distal edge 87 of the cartridge holder assembly 72 by virtue of the spring 201 situated on the proximal end of the locking pin 200. When the needle cartridge 90 is secured to the cartridge holder assembly 72, whereby the grooves 94 are fully engaged with the slots 82, a locking pin recess 202 on the mating surface of the cartridge 90 aligns with the pin 200, allowing the pin 200 to protrude and engage the recess 202, thereby locking the needle cartridge 90 rotationally onto the cartridge holder assembly 72. The locking pin recess 202 is formed to be slightly larger but with a similar cross-sectional shape as the locking pin 200. In one embodiment, the cross-sectional shape of the locking pin 200 and the shape of the locking pin recess 202 are circular. To release the cartridge from the cartridge holder assembly, a user can engage the handle and button 203 attached to the pin 200 and slide the pin 200 proximally to retract it from the locking pin recess 202. Upon retracting the locking pin 200, the user can rotate the needle cartridge 90 to disengage the grooves 94 from the slots 82, and thereby remove the cartridge from the cartridge holder assembly 72. The locking pin recess 202 is more clearly seen in FIG. 12, a perspective view of a portion of the mating or proximal surface of the needle cartridge 90.

The anti-rotate and locking bar 100 engages the outer notch of the needle 110 to prevent rotation of the needle 110 and prevent "needle backing-up" and thereby precluding the needle 110 from straying out of sequence. FIG. 14B shows the needle cartridge 90 locked into position both rotationally and axially.

Figure 13:
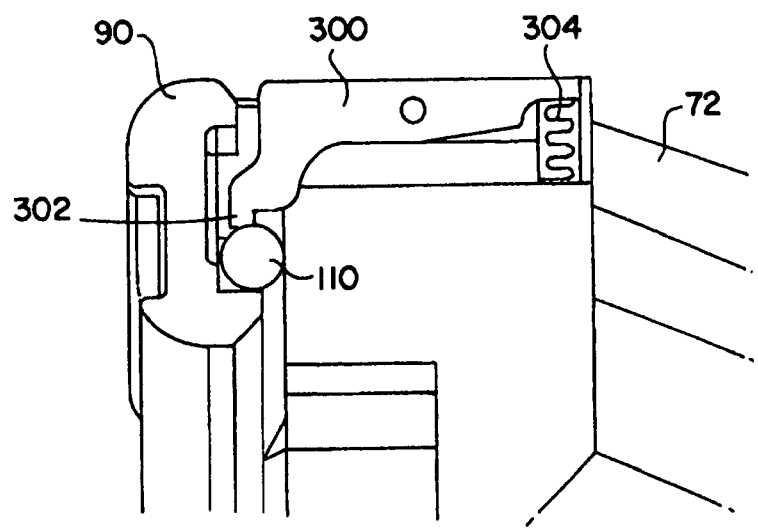
FIG. 13 shows an anti-rotate bar without the locking bar feature, which can be used when the locking pin feature of FIG. 9 is incorporated into the cartridge holder assembly.

The construction of the anti-rotate and locking bar 100 can be simplified if the cartridge locking function is achieved with a locking pin 200. The arm leading to the locking surface 101 of the anti-rotate and locking bar 100, can be eliminated, resulting in a purely anti-rotate bar 300, as shown in FIG. 13. The anti-rotate bar 300 can comprise an anti-rotate surface 302 that makes contact with the needle 110. The anti-rotate bar 300 is biased by spring 304 to engage the anti-rotate surface 302 with the outer notch 116 of needle 110 to prevent reverse rotation of the needle 110.

Figure 15:
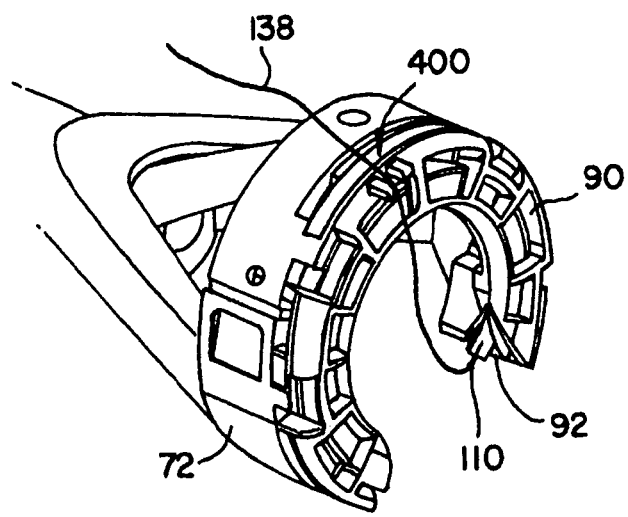
FIG. 15 shows a suture retainer on the top side of the cartridge, used to hold the suture material away from the needle, drive arm and pawl of the needle pusher assembly.
Figure 16:
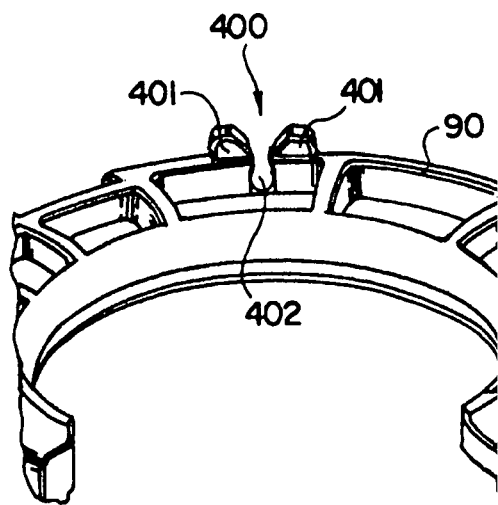
FIG. 16 shows a rearward-leaning perspective view of the front of the cartridge, revealing the recess of the suture retainer of FIG. 15 into which the suture can be placed.
Figure 17:
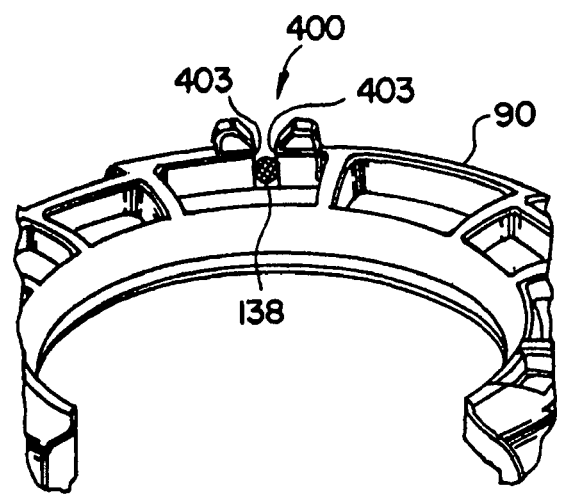
FIG. 17 shows the suture material in cross-section, placed within the recess of the suture retainer of FIG. 15.
Figure 18:
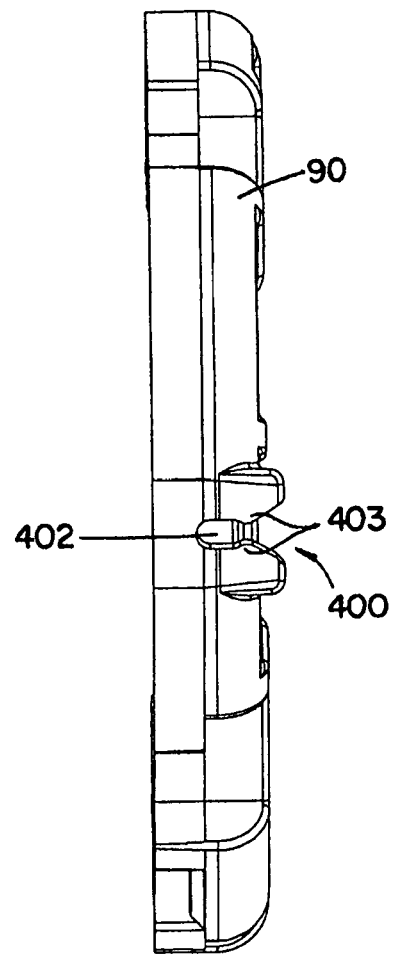
FIG. 18 shows a top view of the needle cartridge and suture retainer of FIG. 15, revealing the detents of the suture retainer projections that hold the suture material within the recess.

As shown in FIG. 15, the cartridge 90 can be equipped with a suture retainer 400 to keep the suture material 138 from interfering with the rotation of the needle 110 during operation of the suturing device 50. The suture retainer 400 helps to keep the suture material 138 away from the needle track 92 of the cartridge 90. A front perspective view of the needle retainer 400 is shown in FIG. 16. The projections 401 help the operator to guide the suture material 138 into the needle retainer recess 402 of the cartridge 90. As shown in FIG. 17, the detents 403 of the needle retainer 400 cause the passageway to the needle retainer recess 402 to be slightly smaller than the diameter of the suture material 138, allowing the operator to press-fit the suture material 138 into the needle retainer recess 402. This is also shown in FIG. 18, illustrating how the detents 403 provide a slightly narrower passageway for the suture material into and out of the needle retainer recess 402. This feature prevents the suture material 138 from unintentionally slipping out of the needle retainer 400.

Figure 19:
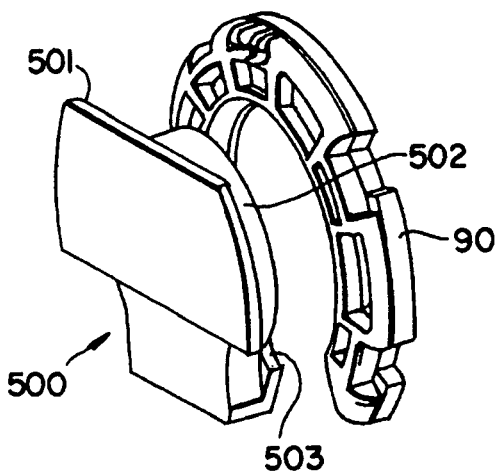
FIG. 19 shows a needle brace that can be installed on the needle cartridge from the outside/distal surface of the cartridge.
Figure 20:
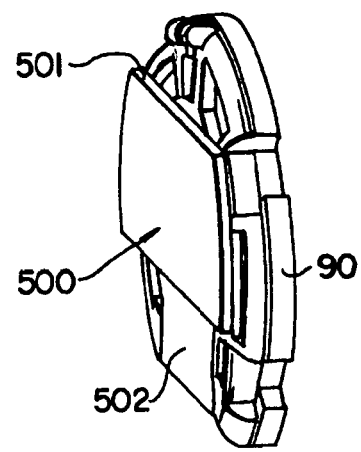
FIG. 20 shows the needle brace of FIG. 19 installed against the needle cartridge.
Figure 21:
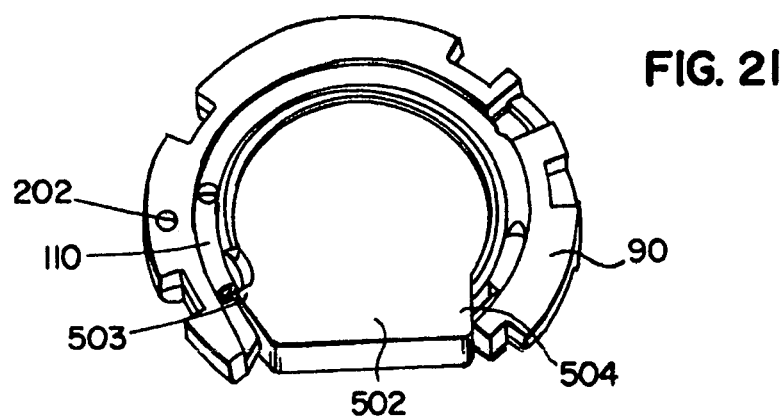
FIG. 21 shows a rear perspective view of the needle brace of FIG. 19 installed in the cartridge, revealing its positioning adjacent to the blunt and pointed ends of the suturing needle.

The needle cartridge 90 can also be equipped with a needle brace 500, as shown in FIG. 19. Positioning a needle brace 500 against the cartridge 90 can prevent inadvertent movement of the needle 110 within the cartridge 90 during handling of the cartridge 90 and suture material 138 prior to loading the cartridge 90 onto the cartridge holder assembly 72. This keeps the needle 110 from straying within the track to a position placing it out of proper sequence for initiation of the first actuation cycle of the suturing device 50. The needle brace 500 has a flange 501 that contacts the outside (distal) surface of the needle cartridge 90 holding the brace in position, as shown in FIG. 20. The needle brace 500 has a body 502 whose outside radial dimension conforms to the inside radial dimension of the cartridge 90, allowing a shoulder feature 503 of needle brace 500 to be situated near the inside (proximal) surface of cartridge 90 and adjacent to the hub or blunt end of needle 110 seated within the cartridge 90, as shown in FIG. 21. The needle 110 is thus prevented from rotating within its track in a reverse direction. Similarly, the pointed end of needle 110 is prevented from moving forward in its track by the presence of the vertical segment 504 of body 502 of needle brace 500, which closely conforms to the inside radial dimension of cartridge 90 and blocks the forward movement of needle 110 in its track. With the needle brace 500 in position, an individual can manipulate the cartridge/needle/suture assembly without fear of inadvertently moving the needle within the track of cartridge 90. Such movement could potentially position the needle out of proper sequence for activation after it is placed on the cartridge holder assembly 72. The needle brace 500 may be formed of a suitable rigid medical grade disposable metal or plastic material.

The needle brace 500 can be secured within the inner circumference of the cartridge 90, either through a frictional 'press' fit, or through tabs placed along the periphery of the needle brace 500, which can cooperate with corresponding depressions (not shown) along the inner circumference of the cartridge 90. In a further refinement of the needle brace 500, the vertical segment 504 can be constructed so that it forms a tab 504A as shown in FIG. 22. The tab 504A is constructed of material with sufficient elastic properties to be somewhat bendable. The Lubricomp plastic material referenced earlier, for example, possesses this characteristic. With the pointed end of needle 110 positioned at the end of the track of cartridge 90, installing needle brace 500 causes the tab 504A to bend slightly and snap into position over the tip of the needle 112, thereby locking the needle brace 500 into position, as shown in FIG. 23. A user can remove the needle brace 500 by applying sufficient force to overcome the elastic resistance of the tab 504a.

Figure 24:
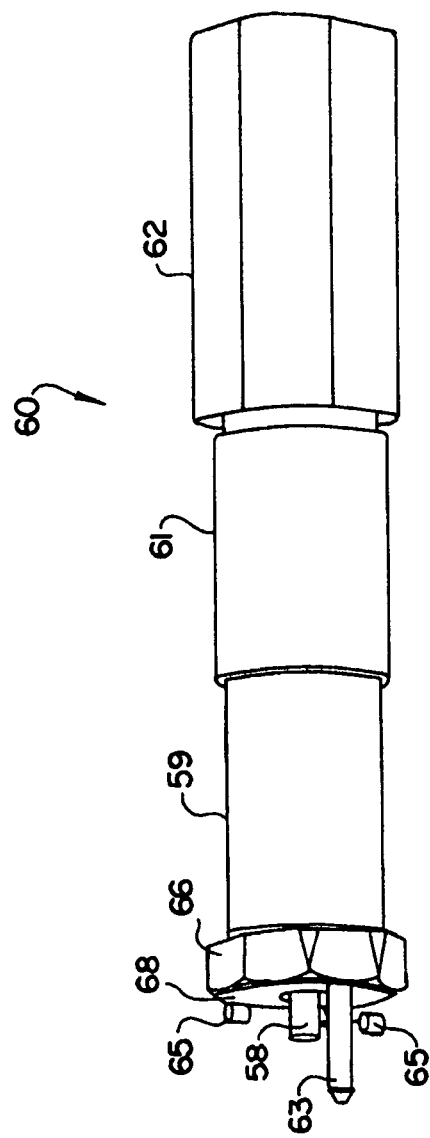
FIG. 24 shows an electronic module of the tissue closure device of FIG. 1.
Figure 25A:
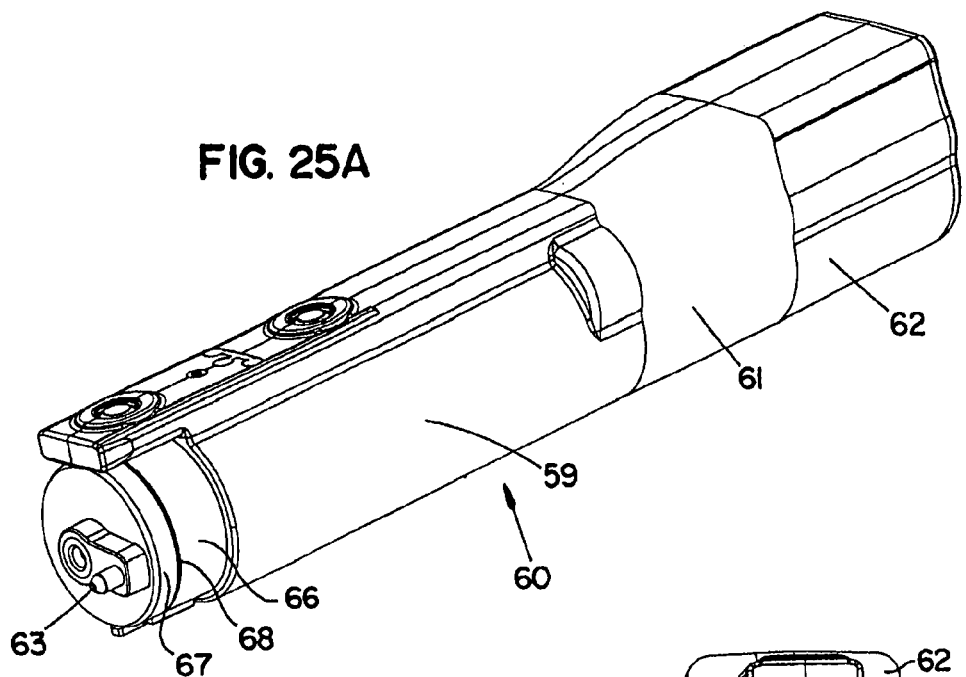
FIGS. 25 A-H show various perspective views of the electronic module of the tissue closure device of FIG. 1, including a left front perspective (A), front perspective (B), right front perspective (C), left rear perspective (D), rear perspective (E), right rear perspective (F), top perspective (G) and bottom perspective (H).
Figure 25B:
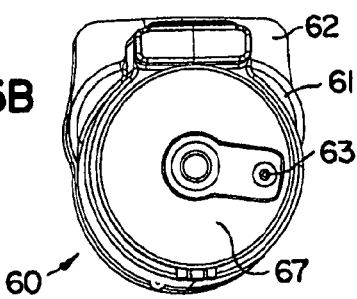
Figure 25C:
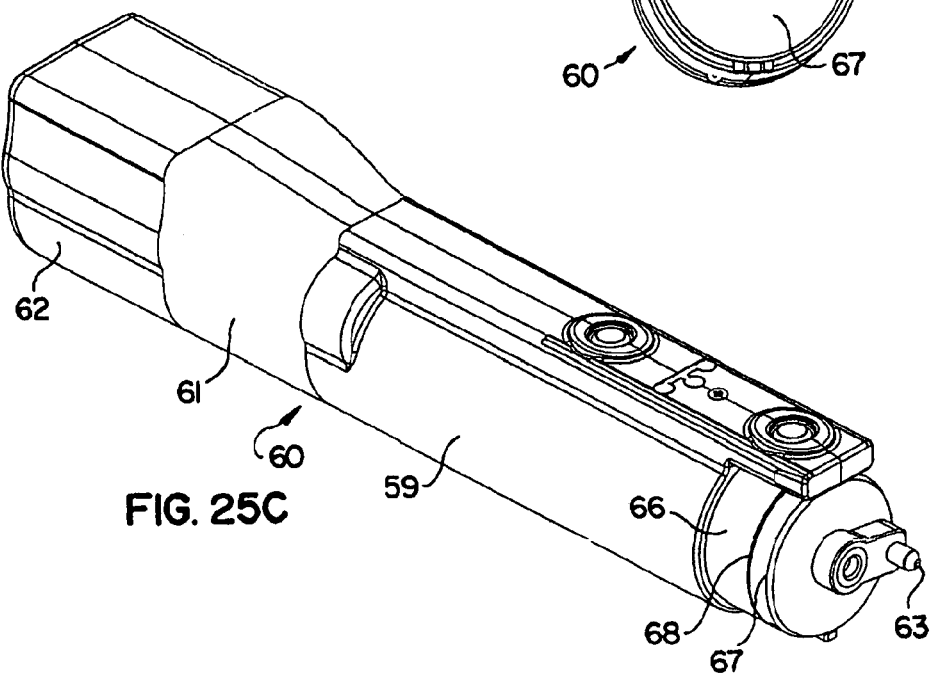
Figure 25D:
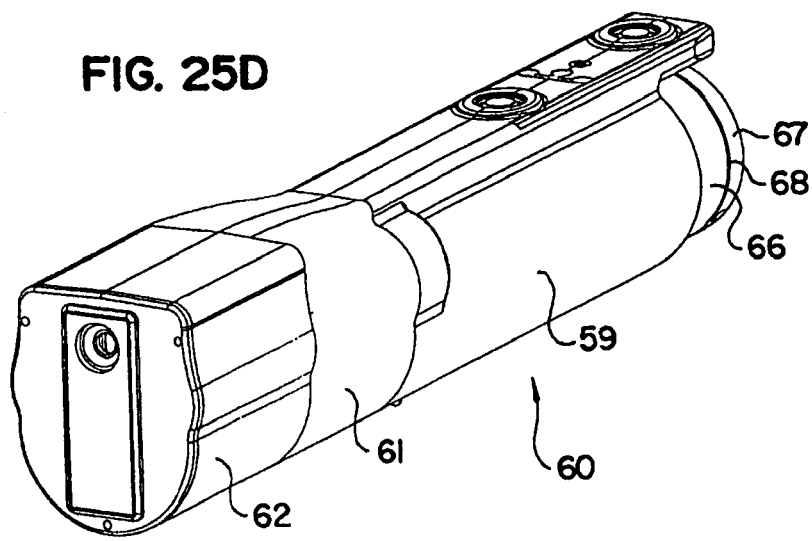
Figure 25E:
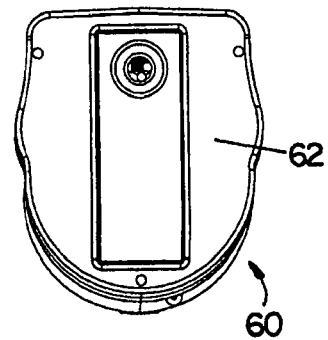
Figure 25F:
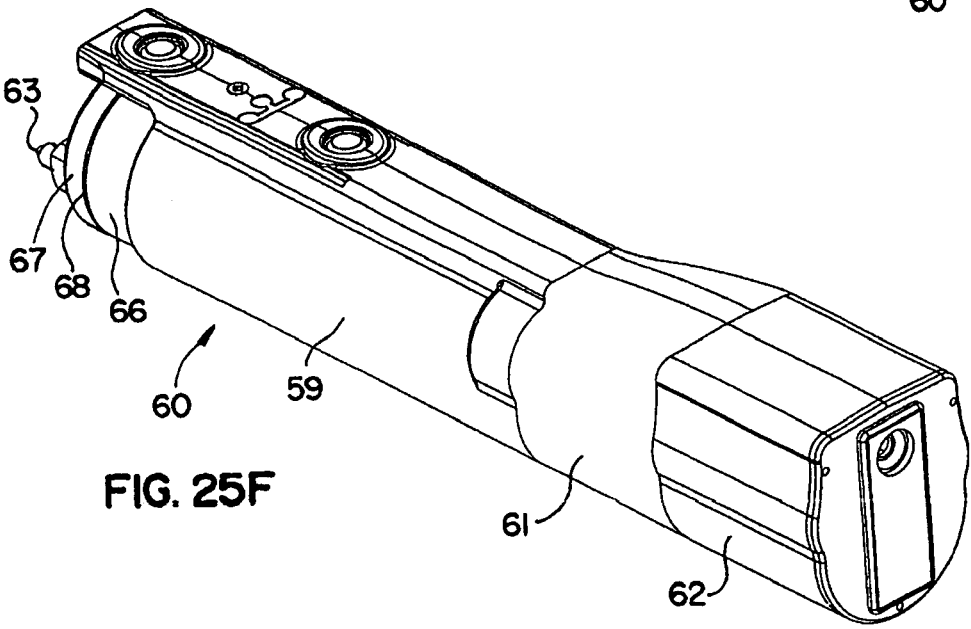

FIG. 24 is an exploded perspective view of the removable electronic module 60 which is a battery-operated electromechanical assembly. The electronic module 60 includes the battery pack 62 and the electric motor 61 which includes the gear box 59 and an output shaft 58, as well as electronic circuits. The battery 62 is preferably re-chargeable and provides the power for the electronic module 60. The battery 62 should have a minimum battery life of about 400 discharge cycles and be able to perform 18 sutures (or 36 total cycles) through a tissue segment such as the sternum. The motor 61 provides the rotational force necessary for the tissue closure device 50 to function. An electronics board controls the operation of the electronic module 60 based on user controlled power and actuation buttons. Indicators are provided to provide feedback to the user of the current status of the electronic module 60. A microprocessor and firmware control the starting, stopping, and torque of the electric motor 61. The electronics also includes the recharging circuit for the battery pack 62. The electronic module 60 may be provided as non-sterile and may be attached to the front end assembly prior to surgery by an aseptic technique. The electronic module 60 may be removed from the front end assembly following a procedure for cleaning, battery charging and storage. Additional views of the electronic module 60 are shown in FIG. 25(A) to 25(H).

Figure 26A:
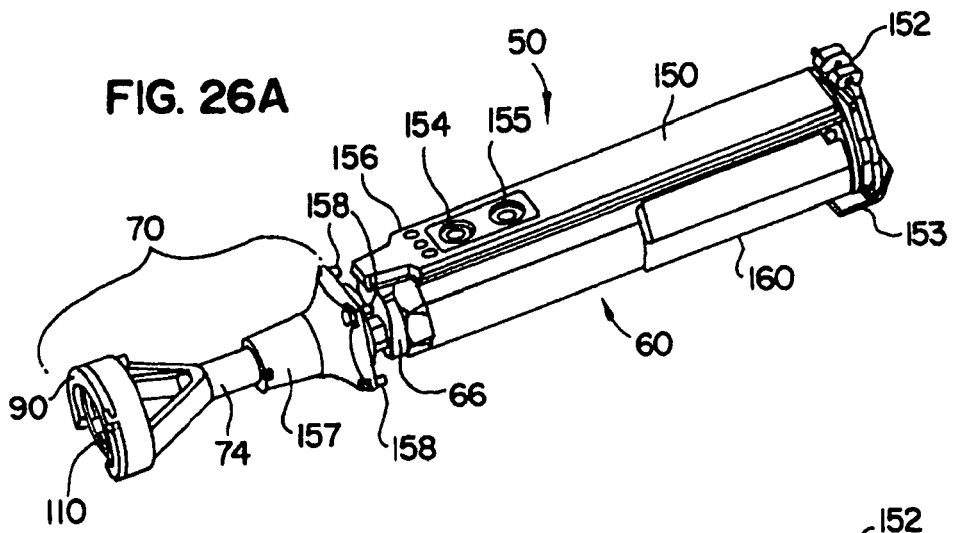
FIG. 26A, FIG. 26B and FIG. 26C show views of a tissue closure device wherein the electronic module has been encased in a housing.
Figure 26B:
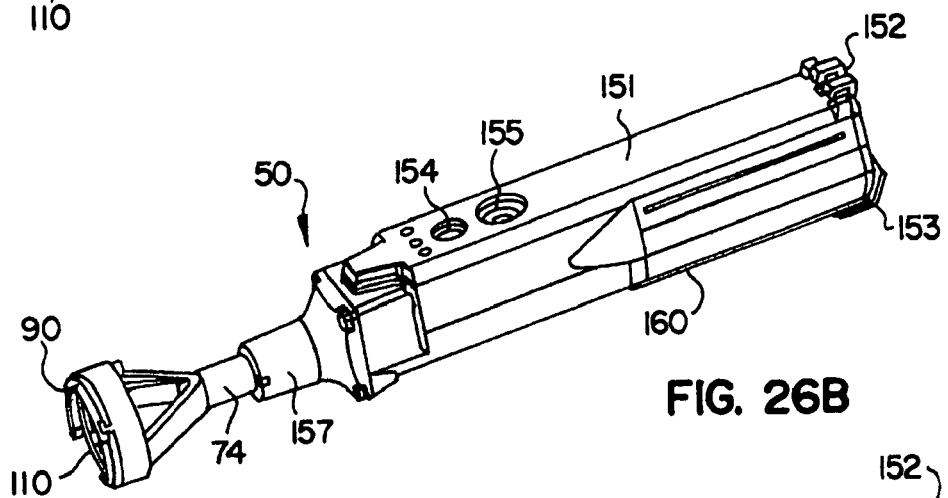

FIGS. 26A and 26B show the tissue closure device 50 wherein the removable electronic module 60 has been enclosed in a thermoplastic enclosure 150 and a thermoplastic housing 151. A door 152, locked by a clamp latch 153, provides entry and exit for the removable electronic module 60. The handle 160 of the device has the door 152 at the proximal end where the removable electronic module 60 is inserted. When the non-sterile battery pack is installed, the door 152 needs to be closed and sealed. The door 152 is sealed using an O-ring or Teflon seal similar to the front end of the device to prevent the egress of any non-sterile germs from the inside the device into the sterile operating field.

Figure 27D:
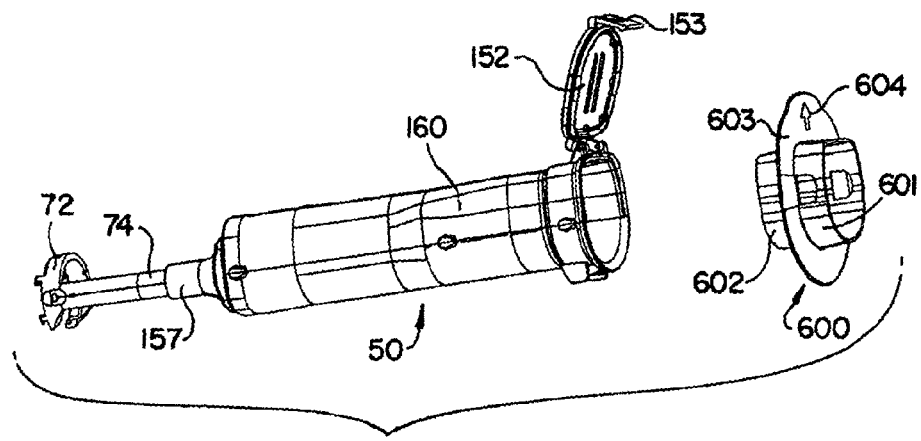
Figure 27E:
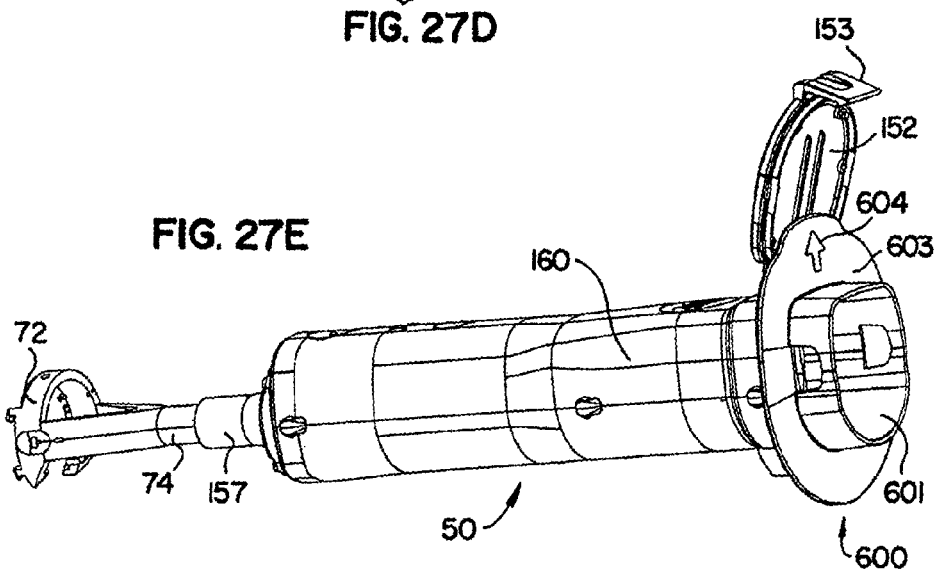
Figure 27F:
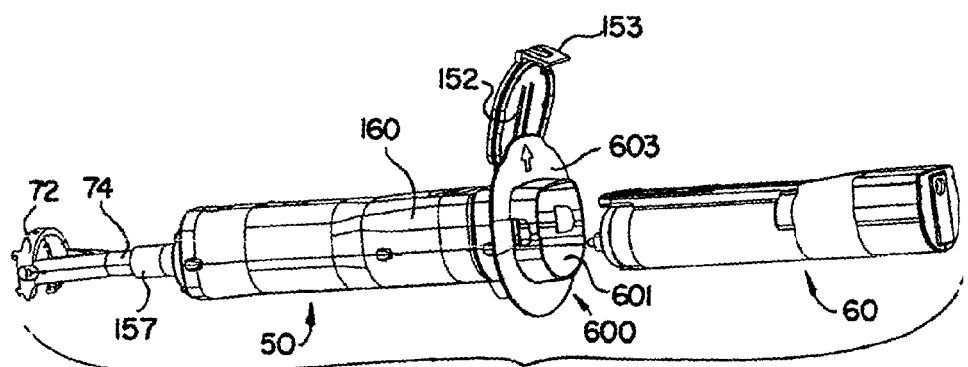
Figure 28A:
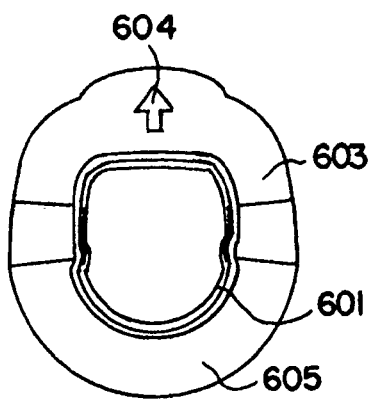
FIGS. 28A-F show various perspective views of the funnel of FIG. 27 in isolation, showing the rear (A), front (B), right side (C), left side (D), top (E) and bottom (F) of the funnel.
Figure 28B:
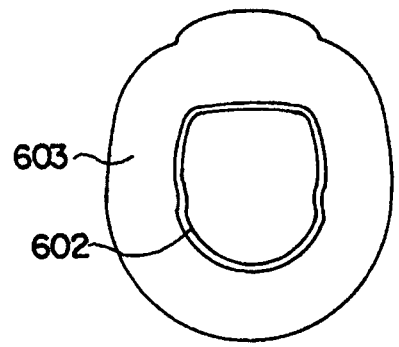
Figure 28C:
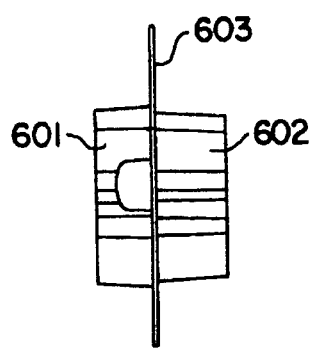
Figure 28D:
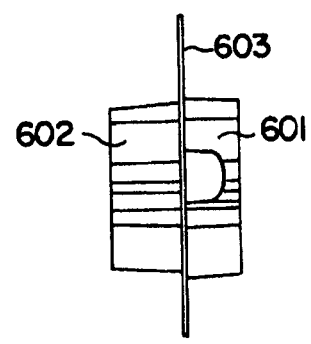
Figure 28E:
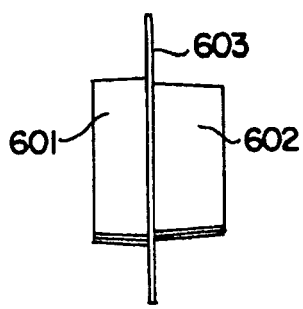
Figure 28F:
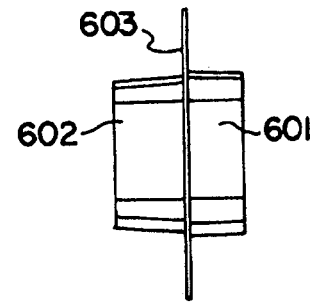

In order to facilitate the placement of a non-sterile electronic module 60 into a sterile handle 160, a funnel 600 can be provided, which is temporarily placed within the opening of the proximal end of the handle 160, as shown in FIGS. 27(A-F). The funnel 600 operates as a physical barrier between the person (e.g. circulating nurse) who handles the non-sterile electronic module 60 and the person (e.g. surgical scrub nurse) who handles the sterile components of the suturing device 50. The sterile components include the handle 160, the door 152, the latch 153, the nose collar 157, the shaft segment 74, cartridge holder assembly 72, and cartridge 90. The funnel 600 is initially sterile when inserted into the handle 160. As shown in FIGS. 28(A-F), the funnel 600 has a proximal barrel 601 and a distal barrel 602, each shaped in cross-section to conform to the cross-sectional shape of the handle 160 and corresponding electronic module 60. The proximal 601 and distal 602 barrels of the funnel 600 are separated by a flange 603 broad enough to form a barrier between the hand of the person inserting the electronic module 60 and the rest of the suturing device 50. An arrow 604 can be printed or engraved on the surface of the flange to direct the user in installing the funnel 600 in the proper vertical orientation. The arrow 604 or other suitable printing 605 on the flange 603 can also help the user distinguish the proximal 601 from the distal 602 barrels of the funnel 600. The distal barrel 602 can fit within the handle 160, as shown in FIGS. 27B and 27E. The electronic module 60 can be passed through the cavity of the funnel 600, as shown in FIGS. 27C and 27F. Once the electronic module 60 has passed through the funnel 600, and has been inserted into the handle 160, the funnel 600 is no longer considered to be sterile and can be removed. The door 152 can then be closed in a sterile manner and secured with the latch 153, also securing the proximal end of the electronic module 60 in place. The outer surfaces of the suturing device 50 remain sterile, a condition facilitated by the use of the funnel 600. In an alternative embodiment, the funnel 600 can have a sterile drape (preferably disposable) attached to the periphery of the flange 603 in order to extend the barrier separating the sterile from the non-sterile components and personnel. The mode of attachment of the drape to the flange 603 can include, for example, a high strength adhesive that resists breakdown by heat, moisture and sterilizing gas.

Figure 26C:
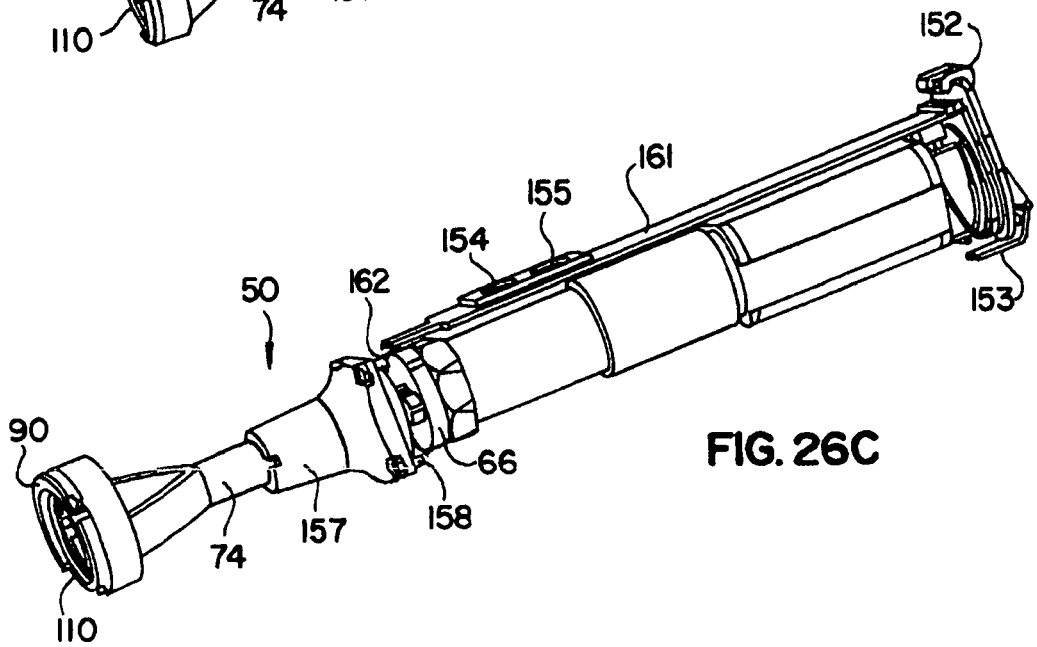
Figure 29:
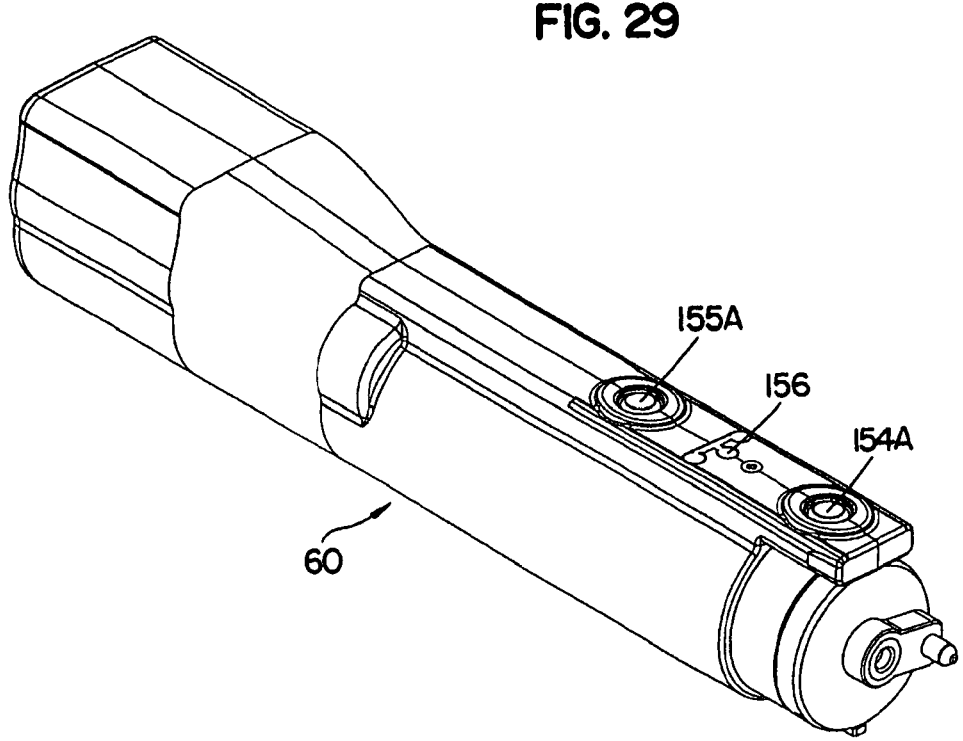
FIG. 29 shows the electronic module of FIG. 25 showing an alternative arrangement of the power and actuation buttons and indicator LED's.

As shown in FIGS. 26A through 26C, a silicone keypad is encapsulated into the enclosure 150 and provides two buttons, one for power 154, and one for actuation 155. An alternative electronic module 60 with a different arrangement of the keypad buttons is shown in FIG. 29, in which the Power-on/Power-off button 154A is separated from the actuation button 155A by the LED indicator 156. The electronic keypad 154A and 155A, and LED indicator 156 are integral to the battery/motor/gear box unit, and form the electronic module 60, as shown in FIG. 29. The Power-on/Power-off button 154 enables the electronic module to either be turned on or off. The actuation button 155 may be depressed which would run the electronic module through one cycle. One cycle consists of a 360° needle 110 rotation accomplished through two 190° rotations of the output shaft 58. The electronic module 60 interfaces with the enclosure 150 through the stop plate 66 mounted to the front of the electronic module 60. The stop plate 66 has flat faces and a taper to engage into the enclosure 150. This provides the connection to capture the torque applied within the unit so that the operator does not have to oppose the torque of the suturing operation (anti-rotation feature). The stop plate 66 also limits the rotation travel of the output shaft 58 to about 190°. A drive wheel is attached to the output shaft of the electronic module 60. The drive wheel contains a drive pin which engages with the drive plate of the front end assembly 70. The drive pin supplies the torque to the front end assembly 70 to drive the needle 110 through the tissue. The drive wheel also contains two permanent magnets. These magnets are preferably used in conjunction with a Hall effect sensor 162 to detect the rotational extents of travel. A nose collar 157 attaches the front end assembly 70 to the housing 151 via screws 158 or some other means for mechanical engagement.

Three indicators (LEDs) 156 show the status of the unit: Power (Green), Error (Red) & Low Battery (Yellow). The housing 151 and keypad provide an exterior surface that is capable of sustaining hospital wipe-down procedures, but is not sterilizable in an autoclave. The electronic module software and operating features cause the needle driver arm to automatically move to its home position (reverse motion limit) when the Power-on/Power-off button 154 is initially activated (depressed). The unit will turn itself off after 10 minutes of inactivity in the event it is stored with the power on. Depressing the Power-on/Power-off button 154 during an actuation cycle will be ignored by the software. When the electronic module is switched On, the On LED indicator will illuminate and remain illuminated until switched Off. In one embodiment, triggering an actuation cycle to drive the needle through tissue by depressing the actuation button 155 will cause the device 50 to automatically power off at the end of the cycle. Once switched On or Off, the electronic module will stay in that condition until deliberately switched to the opposite condition, unless there is an error mode, the electronic module times-out from inactivity, or an actuation cycle has occurred. The electronic module has an Error LED (color red) to indicate an Error Mode. The electronic module also has a Low Battery LED (color Yellow) which indicates the internal battery needs to be charged. The actuation button 155 must be depressed for the device 50 to drive the tissue closure needle 110. The actuation cycle begins when the actuation button 155 is depressed. The actuation button 155 does not have to remain depressed (i.e. the actuation cycle will complete if the button is released). The actuation button 155 only requires one depression to rotate the needle 110 360° (the needle driver arm will automatically rotate 190° twice to accomplish rotating the needle 110 the full 360°) The actuation button 155 is operable so long as the device 50 is On and not already in a suturing sequence. The actuation button 155 must be released and the Power-on button 154 re-depressed before depression of the Actuation button 155 will again begin the next suturing cycle. The electronic Hall effect sensor 162 combined with the firmware sense the extent of the about 190 degree rotations utilizing the permanent magnets in the drive wheel. Once the end of motion is detected the firmware modifies the torque applied to the motor to create a soft-stop. Some of the Error Modes that may occur during operation are listed in Table 1.

TABLE 1

| LED: | Power Green | Error Red | Low Battery Yellow | REM Status: |
|---|---|---|---|---|
| Off Mode | OFF | OFF | OFF | Unit is off and will not actuate |
| On Mode | ON | OFF | OFF | Unit is ready for use |
| Actuating | ON | OFF | OFF | Unit is actuating through a cycle. |
| Error Mode | ON | ON | OFF | Indicates an error occurred. Mechanism will return to home position and not actuate if actuation button is depressed. |
| Recharge Required | ON | OFF | ON | Battery needs to be recharged upon completion of surgery. i.e. unit can do 6 more complete sutures. |
| Battery drained | ON | ON | ON | Battery is drained. Unit will not actuate. Needs to be recharged. |
| Charging Battery | OFF | OFF | Blinking | Charging cycle. Device will not turn on or actuate while in this mode. Blinking rate TBD. |
| Battery Fully Charged | OFF | OFF | ON | Battery charging cycle is completed |

Figure 30:
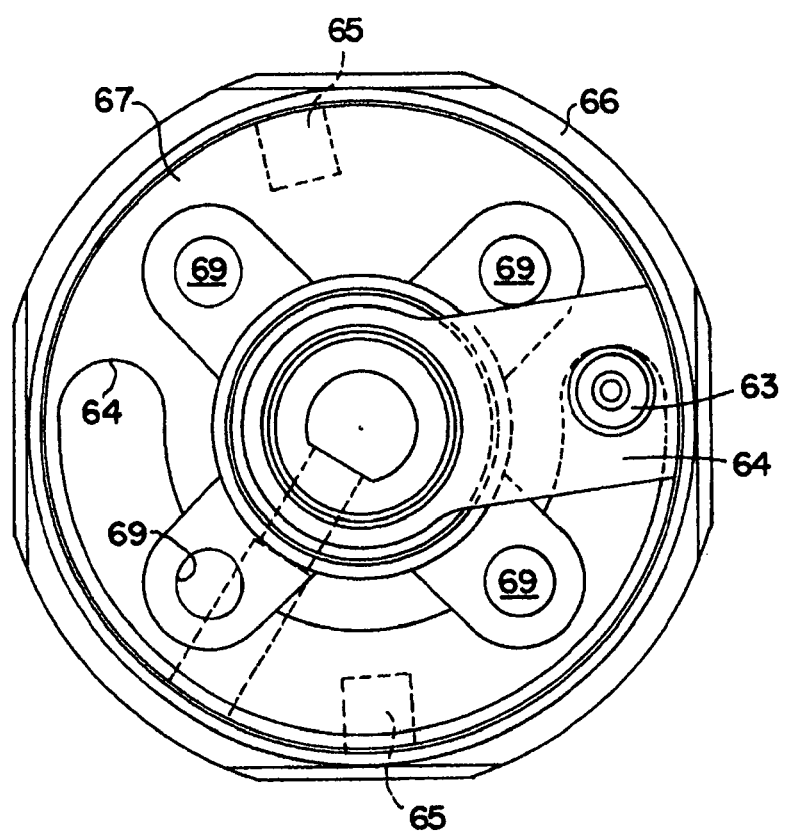
FIG. 30 shows an enlarged view of a drive wheel and a stop plate. A drive pin penetrates the stop plate and rides in a "U-shaped" track.

FIG. 30 is a close-up view of the stop plate 66 and drive wheel 67 (shown as transparent), permanent magnets 65, the drive pin 63 and the gear 59 shaft. At the center of the stop plate 66 there is a hole which provides the entry point for the gear 59 shaft. The stop plate 66 is attached to the gear box 59 by screws 69. The stop plate 66 comprises a "U-shaped" track 64 in which the drive pin 63 rides. As the device is actuated, such that the electronic module causes rotation, the drive pin 63 will ride along the track 64 until the drive pin 63 reaches a stopping point. The track 64 provides the mechanical stops that limit the rotation of the device 50. The permanent magnets 65 are used in conjunction with the Hall effect sensor 162 located at a distal end of an electronics board 161 located inside the removable electronic module 60 to detect the rotational extents of travel. The electronic Hall effect sensor 162 combined with the firmware sense the extent of the about 190 degree rotations utilizing the magnets 65 in the drive wheel 67. Once the end of motion is detected the firmware modifies the torque applied to the motor 61 to create a soft-stop.

FIG. 26C shows the Hall effect sensor 162 located on the electronics board 161 that is used to detect the rotational position of the drive wheel 67. When the rotation is nearing the stopping point, the magnets 65 pass adjacent to the Hall effect sensor 162, sending a signal to the control electronics that the needle 110 will soon be stopping. At that point the motor torque is reduced. The motor continues to drive to the mechanical stopping point at the reduced torque level. When the drive pin 63 hits the mechanical stopping point, the control electronics sense the current spike that is caused by the motor not turning any more and shut off the power to the motor. At least two magnets 65 are positioned in the drive wheel 67 to sense the approach to stopping points at both ends of the arc traveled by the drive wheel 67.

FIGS. 31A and 31B show the main components of the suturing device 50. In FIG. 31A the electronic module 60 has been drawn disengaged from the front end assembly 70. During the disengaged stage, the torsion return spring 77 is extended to allow the pusher assembly 71 to return to a "home" position. In the home position, the drive plate 80 returns to a start position, such that a hole 84 in the drive plate 80 is ready to accept the drive pin 63. As shown in FIG. 31B the electronic module 60 has been attached to the front end assembly 70. When the electronic module 60 is connected, the drive shaft 73 engages a bushing 67a located in the drive wheel 67; the drive pin 63 engages the hole 84 in the drive plate 80 and the device 50 is ready.

FIG. 32A shows the curved suturing needle 110 having a tissue closing material attached. The needle 110 is formed as a circular split ring with the aperture (or gap) 111, the sharp, pointed end 112 and the opposite blunt end 113. The cylindrical bore 114 aligned axially with respect to the needle 110, is located at the blunt end 113. A flexible leader 136 of the tissue closing suture material is inserted into the blunt end 113 and can be restrained by mechanical engagement, for example mechanical crimping. Those skilled in the art will recognize that the flexible leader 136 may engage the needle 110 by any type of mechanical engagement including, but not limited to, welding, soldering, or laser welding. For example, the assembly comprising the flexible leader 136 inserted into the bore 114 of the needle can be immobilized in a clamp, and the junction circumferentially welded with a YAG laser welder or other suitable laser welder. The junction between the flexible leader and wire monofilament suture similarly can be welded or laser-welded. A suture-needle assembly welded in this manner can provide a smoother transition between the needle and flexible leader, and between the flexible leader and the monofilament suture than mechanical crimping, which facilitates drawing the suture material through the tissue. Thus it is easier to pass the suture through the first side of the divided sternum, for example, while maneuvering the device 50 in preparation for placing a suture in the second side of the divided sternum. To enable the needle 110 to penetrate to the required depth, the needle 110 preferably has an arcuate extent between about 250° and about 330°.

Figure 33A:
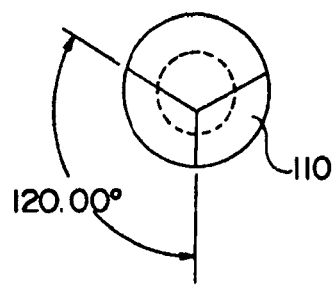
FIGS. 33A-C show details of the construction of the pointed end of the tissue closure needle of FIG. 4, with the distribution of the facets (A), the angle of the outer curvature facet (B), and the resulting shape of the needle point (C).
Figure 33B:
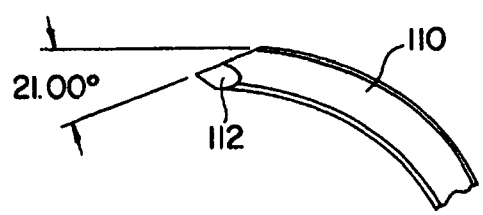
Figure 33C:
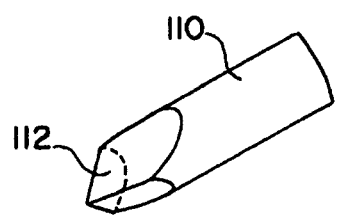

For suturing through bone, it may be preferable to have a triple-faceted (or 'cutting-edge') needle point as shown in FIG. 33A, each facet occupying approximately 120° of the circumference of the needle shaft. As shown in FIG. 33B, One of the facets can be oriented to face the outside curvature of the needle, in which case the outside-facing facet can be cut at a shallower angle than the other two facets, preferably at an angle of approximately 21° with respect to the long axis of the needle shaft. The resulting cutting surface of the needle point as shown in FIG. 33C will have a shorter cutting height, leading to more efficient penetration of bony or other dense tissue. Alternatively, when placing the sutures around the outer or lateral edge of the sternum, the needle tip can be configured with a 'blunt taper-point' or 'ball-point'. The rounded tip and conical shape of the leading component of the needle shaft permits less traumatic penetration through softer tissues. Other applications may require sharper tipped 'taper-point' needles, or even 'reverse-cutting edge' needles.

The needle 110 has two symmetric notches 115a and 115b along the radially rear edge, i.e. the edge proximal to the cartridge holder assembly. The notch 115b is positioned toward the sharp pointed end 112 of the needle 110. The notch 115a is positioned toward the blunt end 113 of the needle 110. The notches 115a and 115b are located opposite to one another, each having a perpendicular (about 90°) segment and an angular segment that makes an angle of about 60° with the perpendicular segment. The notches 115a and 115b are engaged by the drive mechanism (pawl) in the cartridge holder assembly 72 and enable the needle 110 to undergo a rotational movement upon actuation of the drive mechanism, causing the needle 110 to penetrate and advance through the space spanning the split sternum, or other tissue location. A notch 116 is located on the radially outer edge ("outer notch") of the needle 110 proximally to the notch 115b that is closer to the sharp pointed end 112. The outer notch 116 engages with an anti-rotate and locking bar located in the cartridge holder assembly 72, whereby rotation of the needle 110 in a direction opposite to the advancing direction or "needle backing-up" is prevented. The positive engagement of the needle outer notch 116 during operation prevents the needle 110 from straying out of sequence during the suturing process. In addition, the blunt end or hub 113 of the needle 110 can also engage the anti-rotate bar 100 (or 300, if the device has a separate locking pin), as seen in FIG. 39C, to prevent the needle 110 from reversing direction after it has traversed the aperture in the needle cartridge 90.

The needle 110 is enclosed within a cartridge, so the sharp pointed end 112 is not exposed. This needle position, as loaded, is referred to as the "home" position. In the home position, the needle 110 is fully contained within the cartridge housing to eliminate needle-pricks during handling of the cartridge or the loaded device. The width of the aperture in the needle cartridge is comparable to and corresponds with the width of the gap in the needle 110 so that when the needle 110 is in the home position the needle 110 does not project materially into the aperture 111. Such an alignment causes the needle 110 to reside entirely within the needle cartridge, thereby preventing inadvertent contact of the sharp pointed end 112 with the user's fingers during handling of the disposable needle cartridge for placement on the cartridge holder assembly or disposal after use, and while operating the suturing device 50. Such protection of the needle 110 in the suturing device 50 prevents accidental "needle-pricks" from occurring, thereby substantially reducing the risk of infection caused by pathogenic bacteria or viruses that may contaminate the needle 110 during or after use prior to disposal. The needle 110 may be rotated in a curved track of the needle cartridge about the longitudinal axis of the suturing device 50 to advance the pointed needle end 112 so that the needle 110 first spans the aperture 111 and then returns to the home position.

FIG. 32B shows an expanded view of a crimp 137 that houses the ends of the two materials that form a tissue closure suture material. The tissue closing material includes the flexible leader 136 attached to a wire suture 138 by means of the crimp 137. The crimp has an opening on each end, a first opening 137a accepts the flexible leader 136 and a second opening 137b accepts the wire suture 138. The flexible leader 136 is placed into the first opening 137a and then the crimp 137 is mechanically crimped to engage the flexible leader 136. The wire suture 138 is placed into the second opening 137b and then the crimp 137 is mechanically crimped to engage the wire suture 138. Those skilled in the art will recognize that the crimp 137 may engage the flexible leader 136 and the wire suture 138 by any type of mechanical engagement including, but not limited to, welding, soldering, or laser welding. The crimp 137 has a curved shape to make it easier to slide through the holes. The crimp 137 is streamlined and low profile to travel through tissue, cartilage or bone.

Figure 34:
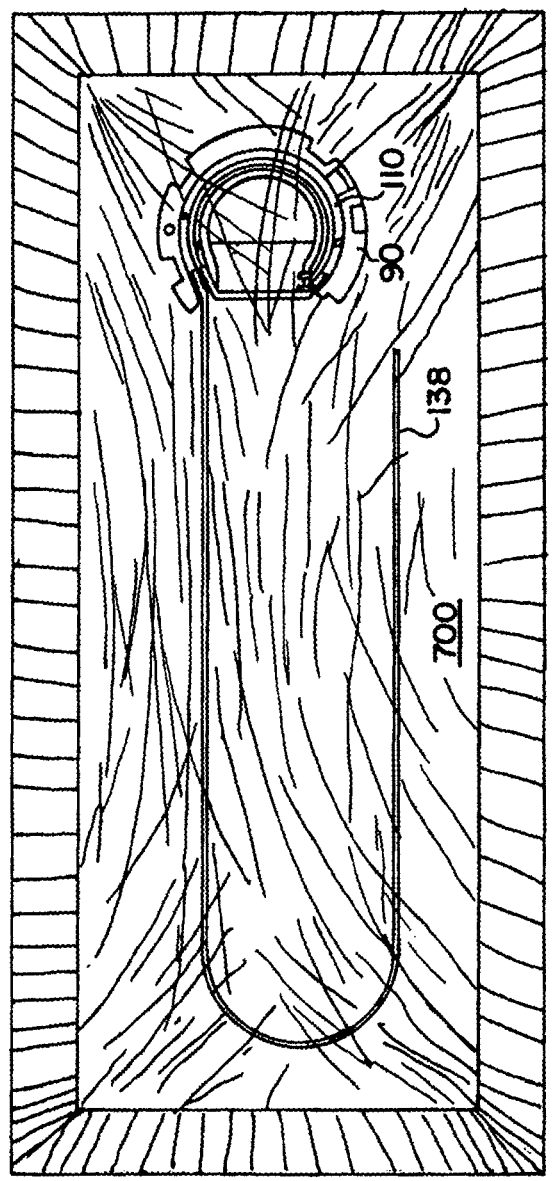
FIG. 34 shows a disposable paper and plastic film package enclosing the sterile needle cartridge of FIG. 7, and the suturing needle and attached suture material of FIG. 32A.

The flexible leader 136 has a diameter (gauge) that is larger or equal to the diameter of the wire suture 138. The flexible leader 136 may be formed from a stainless steel material or by some other braided or monofilament material. In an embodiment, the flexible leader 136 is formed from wire cable. In an embodiment, the length of the flexible leader 136 is between about 8 inches to about 18 inches. The flexible leader 136 may be longer than 18 inches. The flexible leader 136 acts to improve ease of suture manipulation within the thorax, for example (under the sternum) during placement of each of the series of wire sternum closure sutures and thus make sternum closure faster and easier. The wire cable 138 may be formed from wire suture, such as stainless steel, made available in varying wire sizes, such as, for example, 5, 6, and 7. In an embodiment, the length of the wire suture 138 is at least 18 inches and may be longer than 18 inches. As shown in FIG. 34, the cartridge 90, needle 110 and suture material 138 can form the components of a sterile kit, packaged in appropriate plastic/reinforced paper material 700, which preferably can be peeled open to lay out the components onto a sterile field. The bottom web of the package can be thermoformable transparent plastic film, such as polyamide/polyethylene or polypropylene/polyethylene. This allows the contents of the sealed package to be visible. The top web can be sterilizable paper, such as Tyvek®, with a basic weight of about 60 gm/m$^2$ or more, allowing it to be permeable to sterilizing gas, so that the cartridge 90, needle 110 and suture material 138 can be sterilized from within the package. The top and bottom webs are sealed along the periphery of the package using a suitable adhesive. The package preferably can be opened by hand, using peel-open corners and peelable seams.

Figure 35:
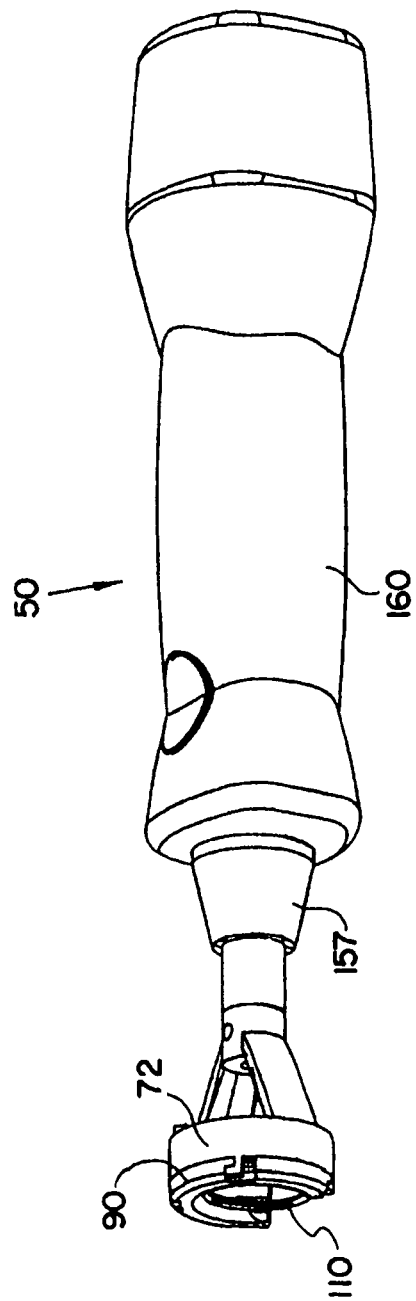
FIG. 35 shows an embodiment of a tissue closure device of the presently disclosed embodiments.
Figure 36A:
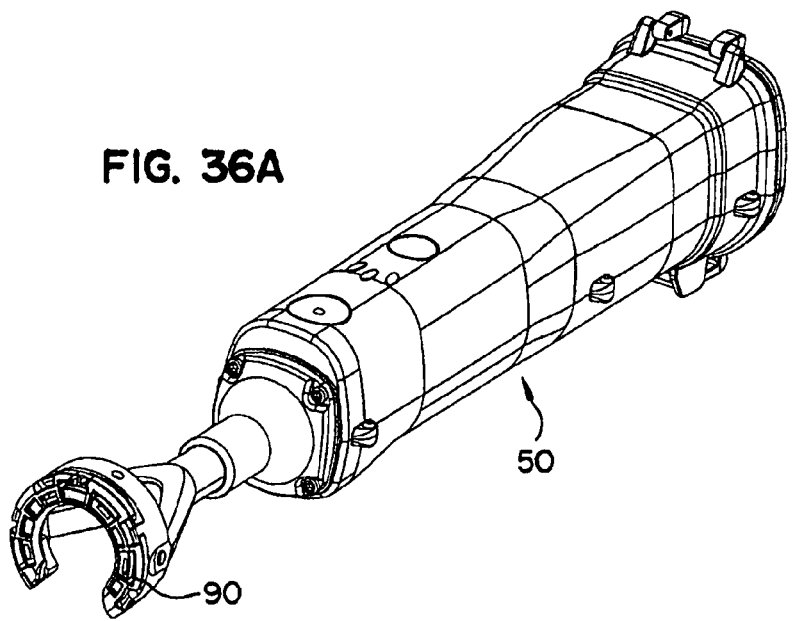
FIGS. 36A-C show front perspective views of an embodiment of the suturing device of FIG. 1, with needle cartridge attached, including left front (A), front (B), and right front (C) perspectives.
Figure 36B:
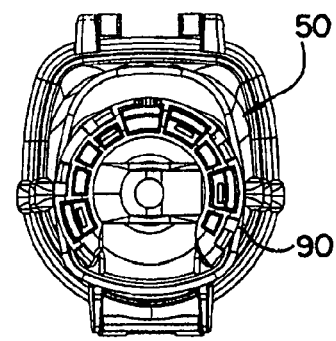
Figure 36C:
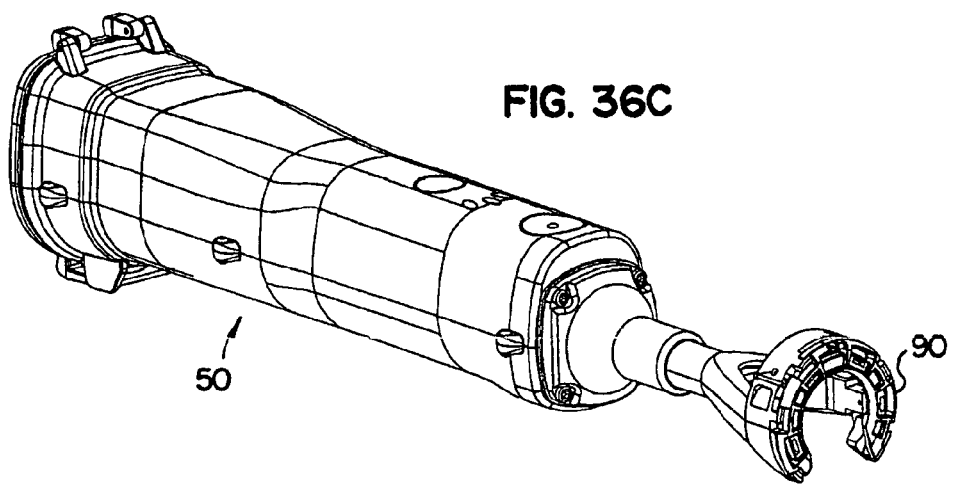
Figure 37A:
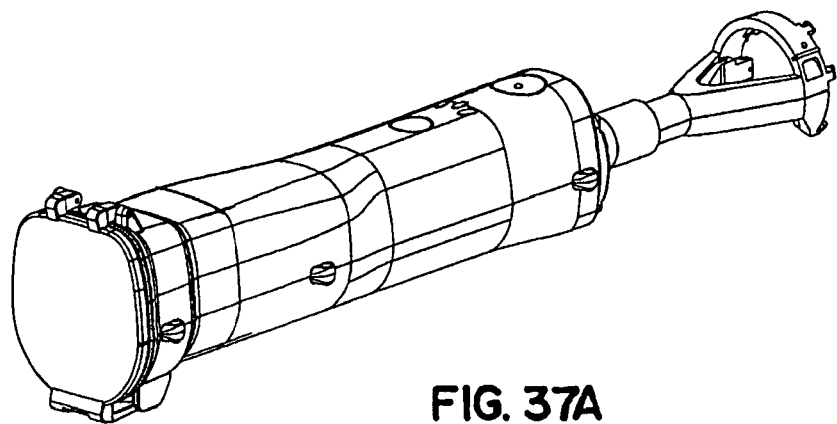
FIGS. 37A-D show other perspective views of the suturing device of FIG. 36, without an attached cartridge, including left rear (A), right rear (B), bottom (C) and top (D) perspectives.
Figure 37B:
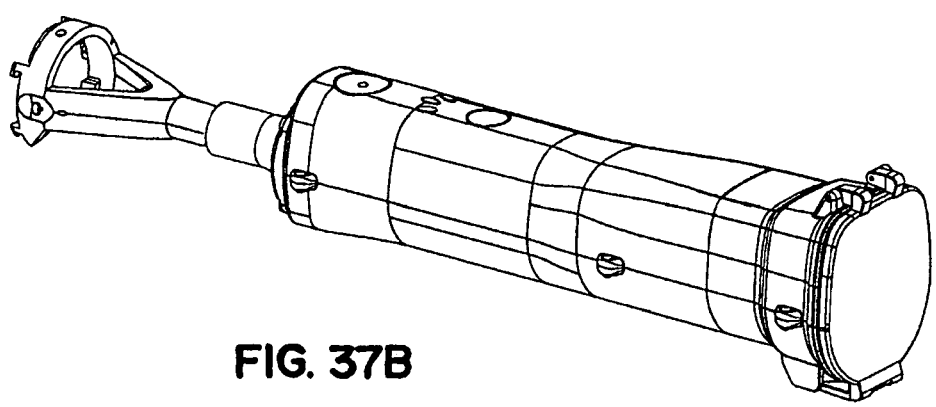
Figure 37C:
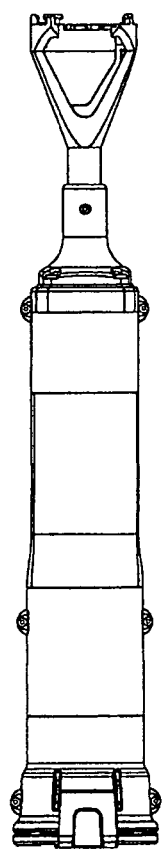
Figure 37D:
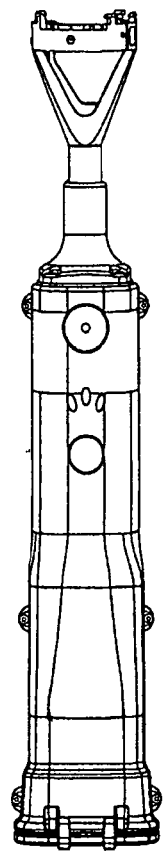
Figure 38:
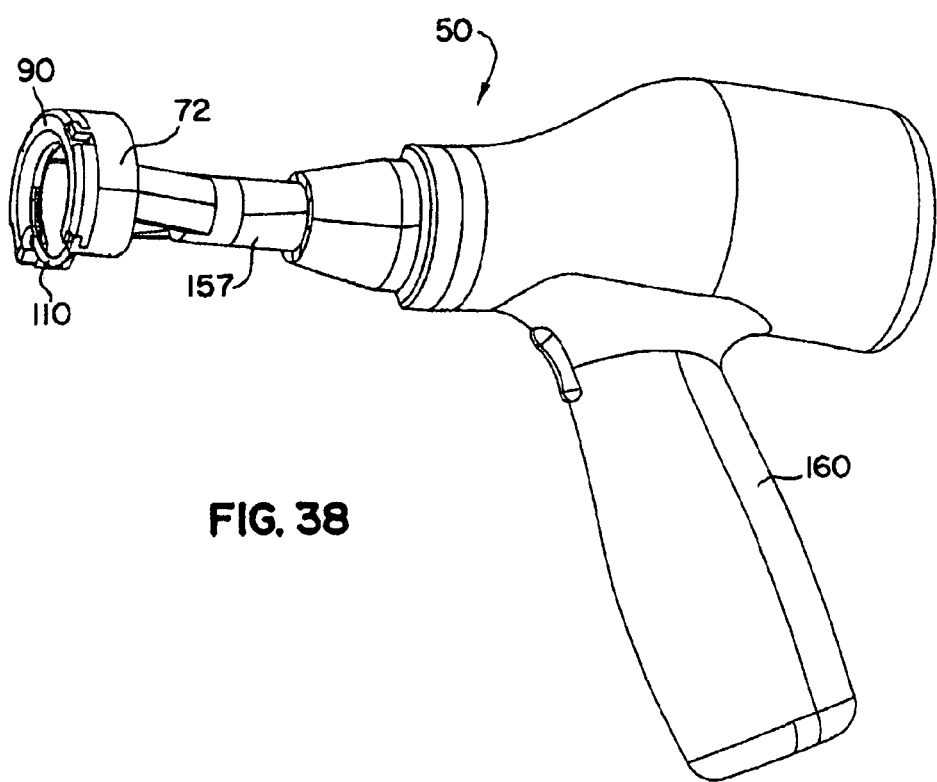
FIG. 38 shows a further embodiment of a tissue closure device provided in accordance with the invention.

The suturing device 50 is designed to be held in the dominant hand of the medical professional. FIG. 35 shows an embodiment of a suturing device having a ergonomic handle 160. FIGS. 36A-C show aspects of the front side of the device 50 with cartridge 90 attached. FIGS. 37A-D show aspects of the rear sides (FIGS. 37A and 37B), the bottom side (FIG. 37C) and the top side (FIG. 37D) of suturing device 50 without the cartridge 90. FIG. 38 shows an embodiment of a suturing device having a pistol-like handle 160. The handle 160 is supplied non-sterile to the medical professional. The hospital or office is responsible for sterilizing the device 50 by techniques known in the art, such as gravity steam sterilization, Steris and ETO. In an embodiment shown in FIG. 35, the electronic module 60 has been surrounded by a hollow handle/body that includes an activator button and may also include flush ports along the handle/body in order to provide a port of entry for cleaning fluids or suction such that the device 50 can be cleaned prior to or after use. In an embodiment shown in FIG. 38, the electronic module 60 has been surrounded by a different hollow handle that includes an activator button and may also include flush ports along the handle/body in order to provide a port of entry for cleaning fluids or suction such that the device 50 can be cleaned prior to or after use. Those skilled in the art will recognize that the battery pack 62 and electric motor 61 can be placed anywhere in the handle and be within the scope and spirit of the presently disclosed embodiments.

Figure 39A:
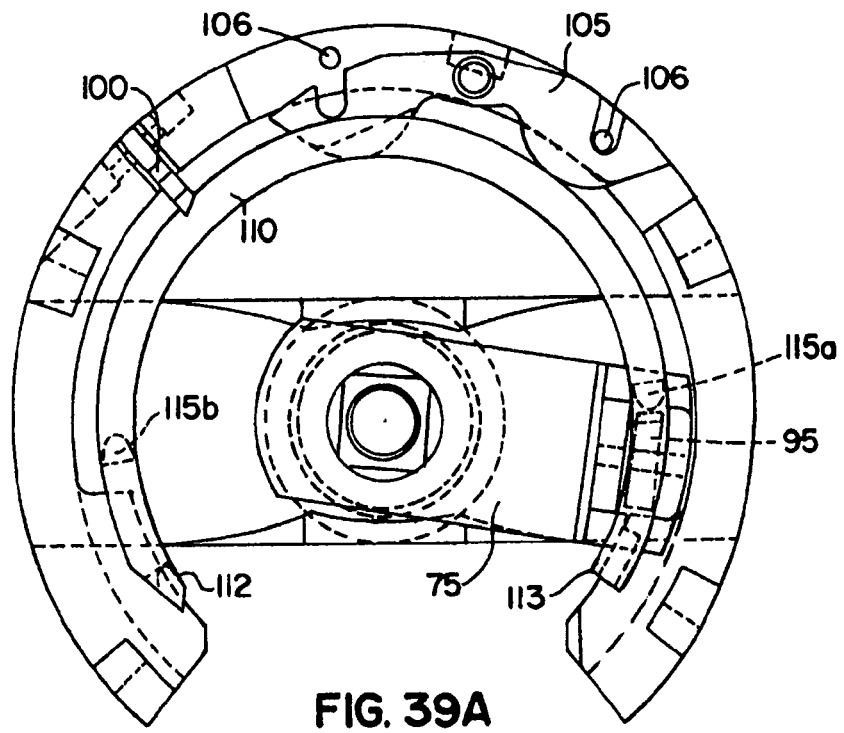
FIGS. 39A-39D shows the operation of the driver arm in the cartridge holder assembly operating in a rear drive mode.
Figure 39B:
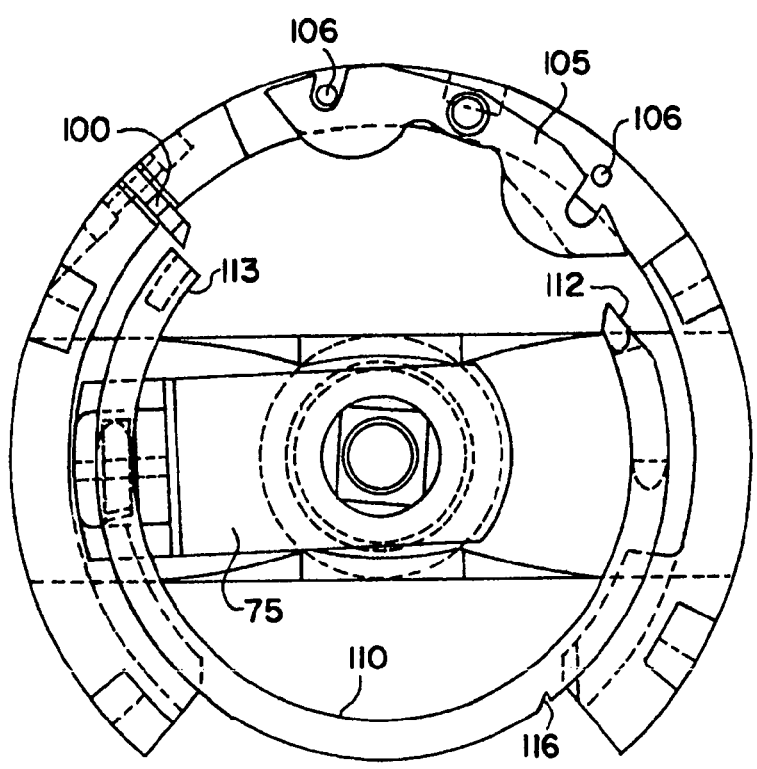
Figure 39C:
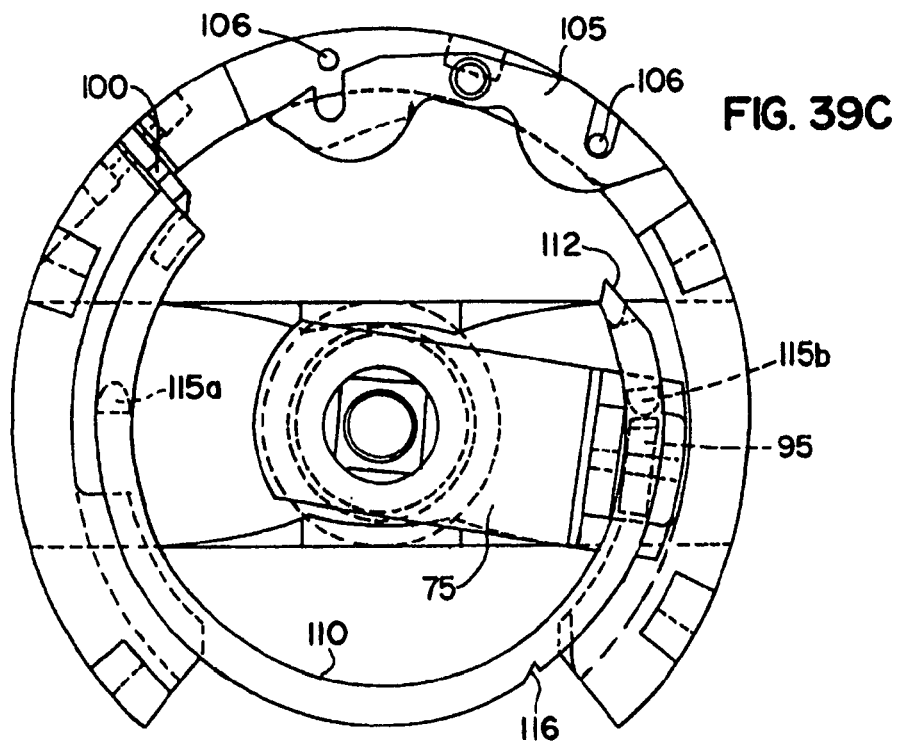
Figure 39D:
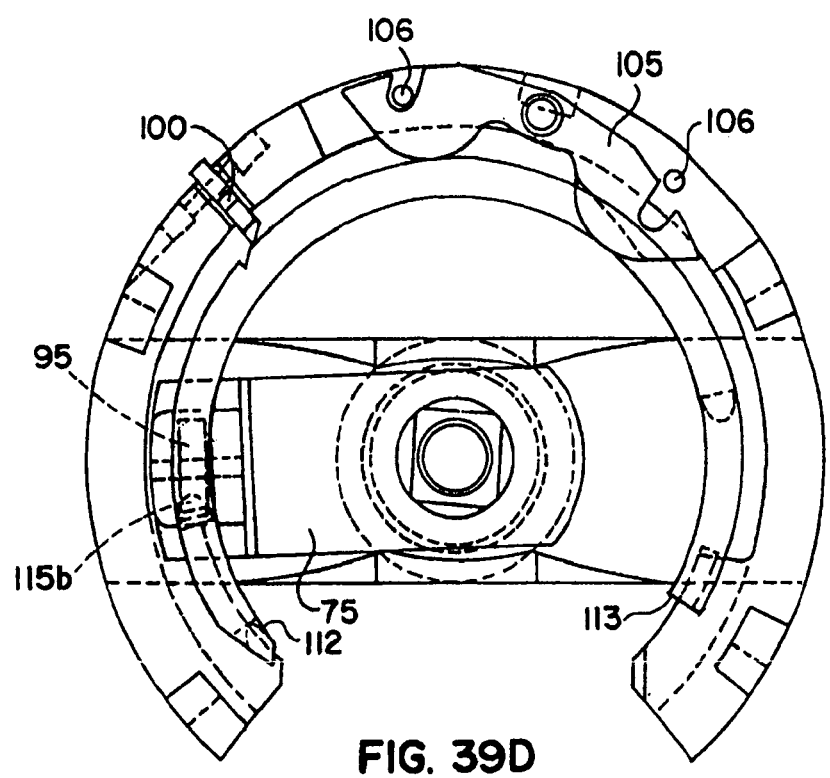

FIGS. 39A, 39B, 39C and 39D show serial views of the "rear-drive" needle operating drive mechanism operating within the distal end of the cartridge holder assembly. The "rear-drive" mechanism comprises the drive arm 75 connected to a drive shaft that is capable of circular motion so as to "sweep" along the circular inner edge of the cartridge holder assembly. FIG. 39A shows the needle 110 in the "home" position. Initially, the pawl 95 has not made contact with the needle 110. The drive arm 75 moves to engage a notch 115a in the needle 110 (referred to as rest position). As shown in FIG. 39B, the gate assembly 105 is resting at stop pin 106. Actuation of the device causes the drive shaft to rotate about 190° in a counterclockwise direction (referred to as position #1), thereby causing the drive arm 75 to move circularly from its "home" rest position and move up to and past the gate assembly 105, causing the gate assembly to pivot clockwise in the process so that the gate assembly 105 is now resting at the other stop pin 106. The needle 110 is prevented from moving backwards by the anti-rotate and locking bar 100. The needle 110, in this position, is referred to as in a "penetrating-state" of the needle 110 cycle. As shown in FIG. 39C, the pawl 95 has been disengaged from the notch 115a and the drive arm 75 continues to move circularly until it comes to rest once again in the "home" position, about 190° clockwise from position #1 (this new position is referred to as position #2). The pawl 95 then engages the notch 115b. The gate assembly 105 has pivoted counterclockwise to rest again at the other stop pin 106. FIG. 39D shows the pawl 95 engaged in the notch 115b and the drive arm 75 continuing to move circularly until it is about 190° clockwise from position #2 (this new position is referred to as position #3). The gate assembly 105 has pivoted clockwise again to rest at stop pin 106. The needle 110 is pulled through the space between the tissue gap (e.g., split sternum) and the closing material follows. The drive arm 75 then returns back to the start home position by rotating 190° clockwise to the position shown in FIG. 39A.

In an embodiment, the handle of the suturing device 50 does not contain batteries, but is powered by electric power provided from outside the sterile field of the operating room (OR). In this external electric power embodiment, the device is configured with an autoclavable motor in the handle and a sterilizable power cord attached to the handle. The device would be connected with the sterilizable cord to a power supply unit that is located outside the sterile field in the operating room. That power unit would be plugged into wall power, and be able to convert the wall power (i.e., 120 volts or 240 volts) to voltage levels appropriate for the motor. The sterilizable cord transmits power to the hand-held unit which contains the motor and the needle driving mechanics. In addition, the control electronics could also be located in the external power unit rather than inside the handle. This change in configuration would reduce the size of the handle.

The suturing device 50 of the presently disclosed embodiments can be used for any procedure in which bony tissue or dense soft tissue closure is required. The tissue chosen should be sufficiently compliant to permit penetration by one of the variety of needle tips that can be used with the device. Other possible uses could include, for example, repair of injuries or incisions involving the attachment points of the rotator cuff, quadriceps tendon, patellar tendon or Achilles tendon, and rib reapproximation after lateral thoracotomy. In some of these cases, it may be advantageous to use non-metallic suture material attached to a needle that is compatible with the cartridge 90, cartridge holder assembly 72, and pusher assembly 71 of the device 50. The non-metallic suture material can include, for example, braided or monofilament nylon, prolene or dacron, natural material such as silk or catgut, and synthetic absorbable material such as polyglycolic acid, polyglactin, polyglyconate or polydioxone.

Using a sternotomy procedure as an example, prior to the procedure, the handle of device 50 is sterilized in a hospital autoclave and delivered to the operating room in the same manner as any other piece of sterile surgical equipment. The battery pack 62 of the electronic module 60 has been charged using a charger and is brought into the non-sterile area of the operating room. As part of the routine set up of the surgical field in the operating room, a surgical scrub nurse will open the sterile package containing the sterilized handle of device 50. The scrub nurse will then open the rear portal of the handle and will use standard practice aseptic technique to present the open portal of the handle to a circulating nurse who is located outside of the sterile operating field. At this time, the scrub nurse can grasp a sterile funnel 600 by the flange 603 and insert it into the handle 160 of the device 50. The circulating nurse will take the fully charged electronic module 60 and install the module 60 into the open rear portal of the handle 160 using standard aseptic technique. The circulating nurse can then grasp the flange 603 of the funnel 600 and withdraw it from the handle 160, being careful not to make contact with any other component of the device 50. To assist in this procedure, the circulating nurse can withdraw the funnel 600 by using a sterile forceps or clamp to grasp the flange 603. The scrub nurse will close the portal, securing and sealing the electronic module 60 into the handle. The reusable device 50 is now ready for the loading of the disposable suture cartridge 90.

When it is time to close the sternum, the scrub nurse will open the sterile disposable suture cartridges 90 that will be used in the case (a typical package will be a 6-pack). One suture cartridge 90 is loaded onto the cartridge holder assembly 72 of the device 50. The device 50 is checked to make sure that the power light 154 is OFF, none of the LED lights 156 should be illuminated. The 10 o'clock and 2 o'clock slots on the needle cartridge 90 are aligned with the 10 o'clock and 2 o'clock tabs on the cartridge holder assembly 72. The needle cartridge 90 is aligned with the cartridge holder assembly 72, pushed onto the cartridge holder assembly 72, and then rotated counterclockwise to lock the needle cartridge 90 in place. The locking pin 200 comes into alignment with the locking pin recess 202 of the cartridge 90, at which point the locking pin 200 can engage the locking pin recess 202. The needle brace 500, if present, can be removed from the cartridge 90 after it has been secured to the cartridge holder assembly 72. The Power On button 154 is then turned on. The green LED will come on, indicating the device 50 is ready. The actuation button 155 is then pressed to cycle the needle 110 once, prior to placing the device 50 in the surgeon's hand. The device 50 should cycle twice, causing the needle 110 to rotate one revolution. The device 50 is now ready to be used to place the first suture. The scrub nurse will hand the device 50 to the surgeon who will perform the suture placement process. Sutures are placed at the surgeon's discretion from top to bottom of the sternum. Typically about six to eight sutures are used to close the sternum. As an additional measure to enhance its operational safety, the device 50 can be programmed to have each actuation cycle require the operator to press the Power-on button 154 before pressing the actuation button 155.

Figure 40:
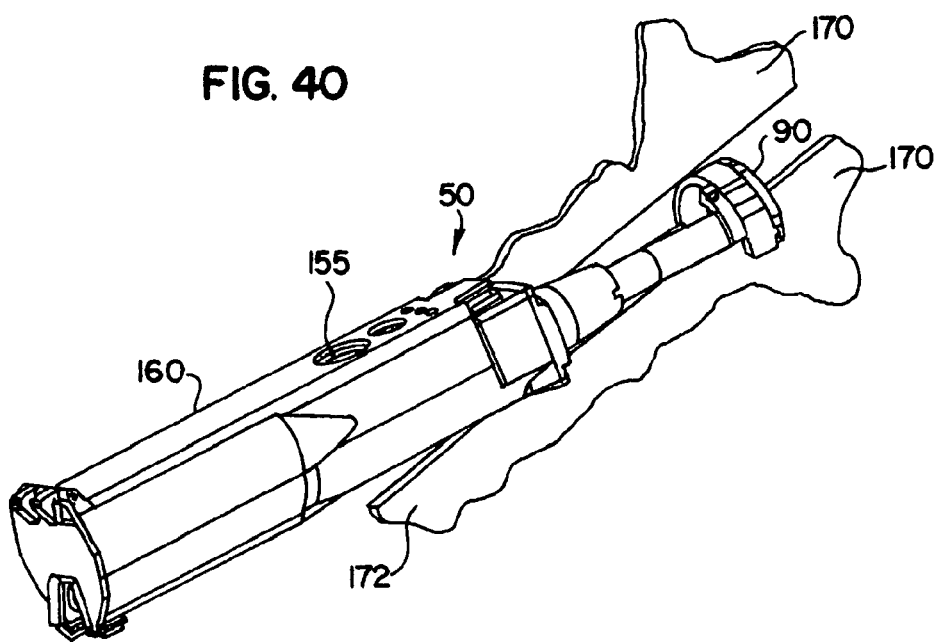
FIG. 40 shows an embodiment of a tissue closure device placed at a sternotomy site such that the device is between a first side and a second side of a split sternum.

To commence the sternotomy closure, any embodiment of the sternotomy closure device 50 is placed at the site of the sternotomy such that the device 50 is between a first side and a second side of a split sternum, the typical starting point is around the manubrium 170 (or head) of the sternum as shown in FIG. 40. The surgeon will elevate one side of the divided sternum with his or her left hand. The surgeon places and aligns the opening (aperture) of the needle cartridge 90 over the cut edge of the sternum locating the penetration point he desires for the suture under the top of the cartridge opening. The surgeon can also use the lower edge of the cartridge holder assembly 72 to elevate the divided sternum during the suturing, obviating the need to place his or her hand under the sternum. The needle will enter the sternum from the exterior (outside) of the patient. The surgeon presses the Power-on button 154 prior to positioning the device 50, and then presses the actuation button 155 while holding the device 50 in the desired location. When the button 155 is pressed, the following actions occur: The electronic controller starts the motor and gearbox rotating clockwise. This motion is transferred from the inside of the electronic module to the drive shaft by the following chain of components: Gearbox shaft to drive wheel to drive plate to the drive shaft to the drive arm. The drive arm holds the pawl. The pawl engages the rear drive notch of the needle. As the drive arm rotates through a first half circular arc, the pawl pushes the needle through a first half of one rotation. This is the stroke that penetrates the sternum. When the drive arm reaches the end of a stroke, the drive arm stops. The drive arm will then reverse direction and return to a start position. As soon as the drive arm reaches the start position, the drive arm stops again. The drive arm now starts to rotate clockwise again. The pawl picks up the front needle notch and pulls the needle through the completion of a stroke. When the drive arm reaches the end of this stroke, the drive arm stops. The drive arm will then reverse direction and return to a start position. As soon as the drive arm reaches a start position, it stops again, and the device 50 automatically powers down. The needle is now completely driven through the one side of the sternum. The flexible leader has been pulled into and through the hole created by the needle. The surgeon will now rotate the device 50 handle clockwise pulling the leader through the one side of the sternum. The surgeon's left hand may be used to assist pulling the flexible leader through the sternum. The surgeon will now elevate the other side of the sternum. The surgeon places and aligns the opening of the needle cartridge 90 over the sternum bone locating the penetration point he desires for the suture under the bottom of the needle cartridge opening. After the surgeon presses the Power-on button 154, followed by the actuation button 155, the needle will enter the sternum from the interior (inside) of the patient. The steps are repeated. At this point, the flexible leader has passed through this side of the sternum. The surgeon may press the cartridge locking surface 101 located on the anti-rotate and locking bar and rotate the needle cartridge 90 clockwise to remove the needle cartridge 90 from the device 50.

The device 50 may be passed to the scrub nurse for loading of a second needle cartridge 90. The surgeon will now use both hands to pull the flexible leader and suture through both sides of the sternum following standard practice for any sternum closure suture. The needle, flexible leader and crimp ferrule are removed from the monofilament suture using standard practices. The surgeon now moves on to place a second suture. The process continues for all remaining sutures that the surgeon chooses to place, typically to an area near the xiphoid process 172. After all desired sutures are placed, the sternum closure is completed using standard surgical techniques. The device 50 may be prepared for cleaning, sterilization and charging. A typical procedure may include: The clean up personnel will wipe down the outside of the device 50 with a disinfectant. The rear portal will be opened and the electronic module will be removed. The electronic module goes to non-sterile equipment storage for charging on the dedicated charger. The device handle will be cleaned to according to a validated cleaning protocol. The device handle will be sterilized according to a validated sterilization protocol.

A Teflon seal 57A or an O-ring seal 57 between the pusher assembly and the cartridge holder assembly 72 provide a sterility barrier so that when the pusher assembly is driving the needle, the drive shaft will rotate within the Teflon seal 57A or O-ring 57 which will prevent anything from migrating down the drive shaft and finding its way inside the handle of the tissue closure device 50.

A method for sternum re-approximation is provided herein. The method includes (a) releasably engaging a cartridge having a protective housing and a suturing needle to a cartridge holder assembly of a sternotomy closure device; (b) placing the sternotomy closure device having the cartridge and the suturing needle to cause an aperture in the cartridge to be between a first side and a second side of a split sternum, wherein a pointed end of the suturing needle is positioned within the protective housing before and after a complete rotation of the suturing needle about a rotational axis; (c) activating an electronic module coupled to a pusher assembly that releasably engages the suturing needle to cause rotational movement of the suturing needle across the aperture in the cartridge and advance the suturing needle through the first side of the split sternum; (d) pulling a suturing material attached to the suturing needle through the first side of the split sternum; and (e) repeating steps (c) and (d) for the second side of the split sternum forming a stitch through the first side and the second side of the split sternum. Steps (b) through (e) are repeated until a length of the first side and the second side of the split sternum have been re-approximated.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims. Thus, it is intended that the present invention include modifications and variations that are within the scope of the appended claims and their equivalents.

What is claimed:

1. A method of directing a needle through a sternum, comprising:
   (a) providing a motorized surgical instrument including:
      (i) a handle having a proximal end and a distal end, the handle defining an enclosable compartment therein, the enclosable compartment being adjustable from an open condition wherein the compartment is exposed to the environment outside the compartment to an enclosed condition wherein the enclosable compartment defines a sterile barrier that isolates the enclosable compartment from the environment outside the compartment;
      (ii) a pusher assembly extending from the distal end of the handle, the pusher assembly having a drive arm extending from a drive shaft and a drive mechanism at a distal end of the drive arm, wherein the drive mechanism is capable of releasably engaging and rotating a split ring suturing needle about a rotational axis through a human sternum; and
      (iii) a removable electronic module that is removably disposable in the enclosable compartment, the enclosable compartment forming a sterile barrier around the removable electronic module when the handle is in the enclosed condition, the removable electronic module being controlled by an actuator that mechanically engages the drive shaft to rotate the drive shaft and the drive mechanism, thereby rotating the suturing needle about the rotational axis, the removable electronic module including:
         a power source for providing power to the electronic module;
         a motor and a gear box adapted to provide a rotational force to rotate the drive shaft and the drive mechanism to rotate the suturing needle; and
         an electronics board that controls operation of the electronic module;
   (b) positioning the motorized surgical instrument so that it surrounds a front portion and a back portion of a sternum; and
   (c) actuating the motorized surgical instrument so that it directs the needle through the sternum.

2. The method of claim 1, further comprising pulling a wire suture through the sternum that is attached to a trailing end of the suturing needle.

3. The method of claim 1, further comprising:
   (a) releasably engaging a cartridge having a protective housing and a suturing needle to a cartridge holder assembly of the motorized surgical instrument;
   (b) wherein positioning the motorized surgical instrument includes positioning the cartridge and the suturing needle to cause an aperture in the cartridge to span said portion of the sternum, wherein a pointed end of the suturing needle is positioned within a protective housing of the cartridge before and after a complete rotation of the suturing needle about a rotational axis, wherein said portion of the sternum is a first portion of the sternum;
   (c) wherein the actuating step includes activating the removable electronic module to in turn actuate the pusher assembly to releasably engage the suturing needle to cause rotational movement of the suturing needle across the aperture in the cartridge and advance the suturing needle through the first bony tissue segment; and wherein the method still further includes:
   (d) pulling a suturing material attached to the suturing needle through the sternum that is attached to a trailing end of the needle.

4. The method of claim 3, further comprising:
   (a) placing the motorized surgical instrument having the cartridge and the suturing needle to cause the aperture in the cartridge to span a second portion of the sternum that is separated from the first portion of the sternum;
   (b) activating the removable electronic module a second time to cause rotational movement of the suturing needle across the aperture in the cartridge and advance the suturing needle through the second portion of the sternum; and
   (c) pulling the suturing material attached to the suturing needle through the second portion of the sternum.

5. The method of claim 4, further comprising re-approximating the first and second portions of the sternum by advancing the first and second portions of the sternum toward each other and holding them together by affixing the suturing material.

6. The method of claim 5, further comprising twist tying the ends of the suturing material together to maintain the re-approximation of the first and second bony tissue segments.

7. The method of claim 6, wherein the suturing material principally includes a metal wire.

8. The method of claim 1, wherein the suturing needle covers an arc greater than about 180° and less than about 330° and has an aperture located adjacent to a blunt second end for engaging a suturing material.

9. The method of claim 1, wherein the electronic module is fully surrounded by an exterior surface of the sternotomy closure device.

10. The method of claim 1, wherein the power source includes a battery pack.

11. The method of claim 1, wherein the power source includes an external power supply connected to a handle by a sterilizable cable.

* * * * *

UNITED STATES PATENT AND TRADEMARK OFFICE
CERTIFICATE OF CORRECTION

PATENT NO. : 9,962,156 B2
APPLICATION NO. : 15/256079
DATED : May 8, 2018
INVENTOR(S) : John C. Meade et al.

It is certified that error appears in the above-identified patent and that said Letters Patent is hereby corrected as shown below:

On the Title Page

Item (72) Inventors:
"Sauliner" should read --Saulnier--

Signed and Sealed this
Twelfth Day of June, 2018

Andrei Iancu
*Director of the United States Patent and Trademark Office*